US012582448B2

(12) United States Patent
Allen et al.

(10) Patent No.: US 12,582,448 B2
(45) Date of Patent: Mar. 24, 2026

(54) STABILIZING BONES USING SCREWS AND RODS

(71) Applicant: GLOBUS MEDICAL, INC., Audubon, PA (US)

(72) Inventors: Caelan Allen, Philadelphia, PA (US); Matthew Bechtel, Philadelphia, PA (US); Noah Hansell, King of Prussia, PA (US); Stefan Lamers, Phoenixville, PA (US); David Leff, Philadelphia, PA (US); David Peretz, Wynnewood, PA (US); George Yacoub, Conshohocken, PA (US)

(73) Assignee: Globus Medical Inc., Audubon, PA (US)

( * ) Notice: Subject to any disclaimer, the term of this patent is extended or adjusted under 35 U.S.C. 154(b) by 489 days.

(21) Appl. No.: 17/704,496

(22) Filed: Mar. 25, 2022

(65) Prior Publication Data

US 2023/0301689 A1     Sep. 28, 2023

(51) Int. Cl.
*A61B 17/70*     (2006.01)
*A61B 17/86*     (2006.01)

(52) U.S. Cl.
CPC ...... *A61B 17/7034* (2013.01); *A61B 17/7032* (2013.01); *A61B 17/7037* (2013.01); *A61B 17/7038* (2013.01); *A61B 17/7082* (2013.01); *A61B 17/8685* (2013.01); *A61B 17/8695* (2013.01); *A61B 17/863* (2013.01)

(58) Field of Classification Search
CPC ............ A61B 17/7032; A61B 17/7034; A61B 17/7037
See application file for complete search history.

(56) References Cited

U.S. PATENT DOCUMENTS

| | | | |
|---|---|---|---|
| 6,843,791 B2 * | 1/2005 | Serhan ............... | A61B 17/7037 606/272 |
| 7,789,900 B2 * | 9/2010 | Levy .................. | A61B 17/7032 606/267 |
| 7,875,065 B2 * | 1/2011 | Jackson ............. | A61B 17/7035 606/301 |
| 8,852,239 B2 * | 10/2014 | Jackson ............. | A61B 17/7038 606/267 |
| 9,271,761 B2 * | 3/2016 | Legallois ............. | A61B 17/704 |
| 9,717,534 B2 * | 8/2017 | Jackson ............. | A61B 17/7053 |
| 9,924,975 B2 * | 3/2018 | Jackson ............. | A61B 17/7037 |
| 10,543,021 B2 * | 1/2020 | Jackson ............. | A61B 17/7037 |

(Continued)

FOREIGN PATENT DOCUMENTS

JP          2013-500127 A        1/2013

*Primary Examiner* — Nicholas W Woodall

(57)          ABSTRACT

An orthopedic fixation device for affixing the screw head of a polyaxial pedicle screw has a tulip, a saddle, and a ring. The tulip has an interior cavity and two opposed threaded arms and a lower ledge. The saddle is inserted into the tulip body, and has a U shaped groove for receiving a spinal fixation rod. The ring has a diameter that is smaller than the widest diameter of the screw head, and is formable into a diameter larger than the widest diameter of the screw head when the screw head is pushed into the ring. The ring has a connection portion that mates with a connection portion of the saddle. The screw head is clamped within the tulip body between the saddle and the ring when a cap is threaded between the tulip arms.

4 Claims, 11 Drawing Sheets

(56)          References Cited

U.S. PATENT DOCUMENTS

| 12,053,209 | B2 * | 8/2024 | Jackson | ............ A61B 17/7037 |
|---|---|---|---|---|
| 2004/0267264 | A1 * | 12/2004 | Konieczynski | .... A61B 17/7032 |
| | | | | 606/289 |
| 2008/0015579 | A1 | 1/2008 | Whipple | |
| 2011/0098755 | A1 | 4/2011 | Jackson et al. | |
| 2013/0096622 | A1 | 4/2013 | Biedermann et al. | |
| 2015/0201972 | A1 | 7/2015 | Doubler et al. | |
| 2016/0331412 | A1 | 11/2016 | Biedermann et al. | |
| 2018/0243010 | A1 | 8/2018 | Murabayashi et al. | |

* cited by examiner

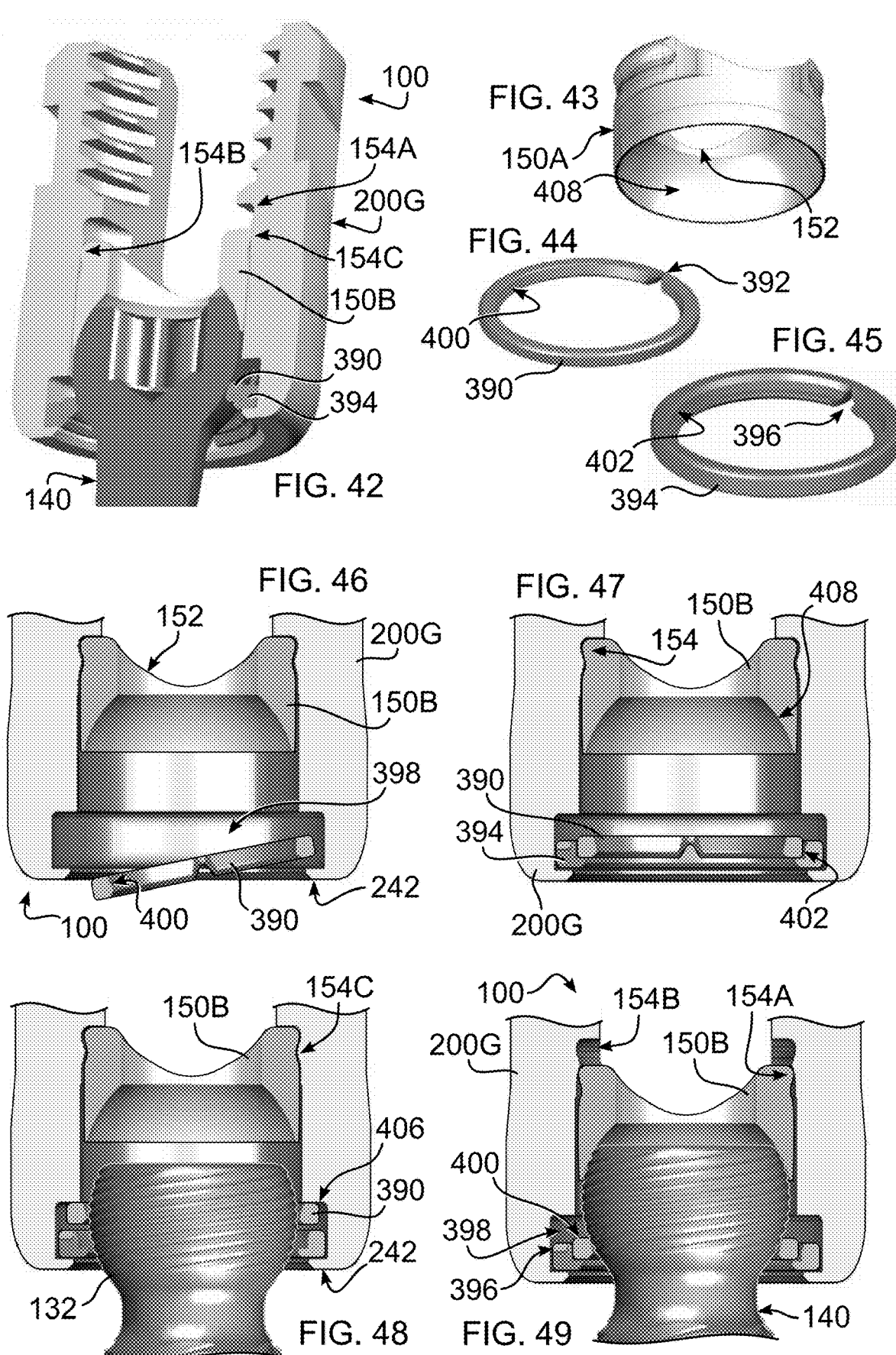

STABILIZING BONES USING SCREWS AND RODS

FIELD OF THE DISCLOSURE

This disclosure relates to stabilizing bones using screws and rods, and more particularly to screws with multiple threads and attaching modular fixation heads ("tulips") after screw insertion.

BACKGROUND OF THE DISCLOSURE

Many types of spinal irregularities cause pain, limit range of motion, or injure the nervous system within the spinal column. These irregularities may result from, without limitations, trauma, tumor, disc degeneration, and disease. Often, these irregularities are treated by immobilizing a portion of the spine. This treatment typically involves affixing a bone screw to one or more vertebrae and connecting the bone screws to an elongate spinal rod that stabilizes members of the spine.

The screw may be a pedicle screw having a tulip head for coupling the screw to the elongate spinal rod. There exists a need for improved designs of the screws, instruments for implantation, and enhanced methods for placement and assembly of the devices.

SUMMARY OF THE DISCLOSURE

In an embodiment of the disclosure, an orthopedic fixation device for affixing the screw head of a polyaxial pedicle screw, includes a tulip defining a distal and proximal end and forming a tulip body forming an interior cavity, two opposed arms extending away from a proximal end of the body, cooperating threads disposed on mutually facing sides of each arm, and a ledge positioned at a distal end of the tulip body at an entrance to the cavity; a saddle defining a distal and proximal end, the saddle sized and dimensioned to be insertable into the tulip body, forming a U shaped groove on the saddle proximal end sized to receive a spinal fixation rod inserted between the tulip arms, and forming a curved surface on the saddle distal end sized and dimensioned to conformingly receive the screw head; and a ring for engaging the screw head, the ring positionable to form a first diameter smaller than the widest diameter of the screw head, positionable to form a second diameter larger than the widest diameter of the screw head when the screw head is passed into the ring, and positioned upon a proximal side of the tulip ledge; the screw head clampable within the tulip body interior cavity in a position between the saddle and the ring when the saddle is urged in a distal direction towards the tulip ledge.

In a variation thereof, the saddle is insertable into a distal end of the tulip body.

In another variation thereof, the device further includes a retaining ring positionable upon a proximal side of the tulip ledge, having a diameter larger than the diameter of the tulip ledge, and forming a ring engaging profile having a diameter smaller than a diameter of the tulip ledge; whereby the ring presses against the profile when the saddle is urged in a distal direction, to thereby prevent the ring from moving out of the cavity.

In a further variation thereof, the retaining ring has a gap formed therethrough, the retaining ring thereby insertable past the tulip ledge by winding the retaining ring past the tulip ledge; the tulip additionally forms a detent portion positioned distal to the threads upon an interior surface of the cavity, and the saddle additionally forms a detent portion mateable with the detent portion of the tulip to mutually releaseably connect the tulip and the saddle.

In a still further variation thereof, the saddle further includes a plurality of distally extending arms, the ring including at least two segments positionable mutually apart to form the second diameter when the screw head is passed therebetween, and the at least two segments being urged mutually together by the plurality of distally extending arms to position the at least two segments into the first diameter when the saddle is urged in a distal direction; and/or the tulip interior cavity includes tulip detent portions, and each of the at least two segments include clip detent portions mateable with the tulip detent portions to releasably retain the at least two segments apart to facilitate insertion of the screw head.

In further variations thereof, the ring is a torsion ring having cam lobes which engage the screw head to twist the ring and deflect the cam lobes to expand a diameter of the ring as the screw head is passed through the ring; the ring is integrally formed with the saddle, the saddle rotatable to form the second diameter to admit passage of the screw head into the saddle; the tulip ledge is formed as two intersecting openings having relatively different diameters; a set screw blocks rotation of the saddle after the saddle has been rotated to form the first diameter to engage the screw head; and/or wherein the ring is sheared as the screw head is passed through the ring to thereby expanded a diameter of the ring.

In another variation thereof, the ring: forms a peripheral axially extending profile forming a plurality of peripheral kerfs extending partially along the length of the of the axially extending profile, forms a ledge peripherally extending radially about, and extending inwards towards, an axial center of the ring, and includes a plurality of kerfs extending through the ledge enabling the ledge to form the second diameter.

In another variation, the device further includes a retaining ring: positionable upon a proximal side of the tulip ledge, having a diameter larger than the diameter of the tulip ledge, and forming a ring engaging profile having a diameter smaller than the diameter of the tulip ledge and dimensioned to receive the ring ledge and prevent the ring ledge from forming the second diameter.

In a further variation, the tulip: includes a second detent portion within the cavity, distal to the detent positioned distal to the threads; and the ring: forms a peripheral axially extending profile forming a plurality of peripheral kerfs extending partially along the length of the of the axially extending profile, forms a ledge peripherally extending radially about, and extending inwards towards, an axial center of the ring, includes a plurality of kerfs extending through the ledge enabling the ledge to form the first diameter and the second diameter, and forms a detent peripherally disposed about a proximal end of the ring, mateable with the second detent portion of the tulip.

In other variations thereof, the ring forms one or more axially extending kerfs; the tulip including at least one radially extending pin, the pin extending into a kerf of the ring as the ring is moved axially, the pin thereby guiding movement of the ring and blocking movement of the ring beyond an axially extending length of the kerf; and/or at least one kerf extending from a proximal surface of the ring and extending axially to a length less than an axial length of the ring, and at least one kerf extending from a distal surface of the ring and extending axially to a length less than an axial length of the ring, the ring thereby compressible about a proximal periphery and compressible about a distal periphery.

In yet further variations thereof, the ring includes a plurality of serrations on an exterior surface cooperative with an interior surface of the tulip cavity to reduce movement of the ring when a screw head is clamped; the plurality of serrations are disposed at an angle that is offset with respect to a central axis of the ring; the ring includes a radially extending flange, the tulip including a radially extending flange, the flange of the ring and the flange of the tulip engageable as the ring is moved axially to define an extent of axial movement of the ring; and/or the radially extending flange of the ring formed as a plurality of flexible digits each having at a free end a flange portion.

In another variation thereof, the ring forming one or more axially extending kerfs, the one or more kerfs enabling expansion of a distal peripheral end of the ring, the retaining ring including an internal profile shaped to contain the distal peripheral end of the ring and block expansion of the distal peripheral end of the ring when the distal peripheral end of the ring is seated within the internal profile; the ring engaging profile is disposed distally to the tulip ledge when the retaining ring is positioned upon the tulip ledge.

In another embodiment of the disclosure, an orthopedic fixation device for affixing the screw head of a polyaxial pedicle screw includes a tulip defining a distal and proximal end and forming a tulip body forming an interior cavity, two opposed arms extending away from a proximal end of the body, cooperating threads disposed on mutually facing sides of each arm, and a ramp positioned at a distal end of the tulip body at an entrance to the cavity; a saddle defining a distal and proximal end, the saddle sized and dimensioned to be insertable into the tulip body, forming a U shaped groove on the saddle proximal end sized to receive a spinal fixation rod inserted between the tulip arms, forming a mating connection portion on peripheral surface of a distal end; and a ring for engaging the screw head, the ring having a first diameter smaller than the widest diameter of the screw head, formable into an second diameter larger than the widest diameter of the screw head when the screw head is passed into the ring, including a mating connection portion mateable with the mating connection portion of the saddle, whereby the ring and the saddle are mutually releaseably connectable, and having a ramp cooperative with the ramp of the tulip; the screw head clampable within the tulip body interior cavity in a position between the saddle and the ring when the saddle is urged in a distal direction towards the tulip ledge and the ramp of the ring slides against the ramp of the tulip.

In variations thereof, the saddle is insertable into a distal end of the tulip body; the saddle and connected ring are insertable into a distal end of the tulip body when the saddle and ring are mutually connected; the tulip additionally forming a detent portion positioned distal to the threads upon an interior surface of the cavity, and the saddle forming a detent portion on a proximal end mateable with the detent portion of the tulip to mutually releaseably connect the tulip and the saddle; the ring forms one or more axially extending kerfs; the one or more axially extending kerfs dividing the ring into segments; the tulip includes at least one radially extending pin, the pin extending into a kerf of the ring as the ring is moved axially, the pin thereby guiding movement of the ring and blocking movement of the ring beyond an axially extending length of the kerf; and/or at least one kerf extending from a proximal surface of the ring and extending axially to a length less than an axial length of the ring, and at least one kerf extending from a distal surface of the ring and extending axially to a length less than an axial length of the ring, the ring thereby compressible about a proximal periphery and compressible about a distal periphery.

In other variations thereof, the ring includes a plurality of serrations on an exterior surface cooperative with an interior surface of the tulip cavity to reduce movement of the ring when a screw head is clamped; the plurality of serrations are disposed at an angle that is offset with respect to a central axis of the ring; the ring includes a radially extending flange, the tulip includes a radially extending flange, the flange of the ring and the flange of the tulip are engageable as the ring is moved axially to define an extent of axial movement of the ring; the radially extending flange of the ring is formed as a plurality of flexible digits each having at a free end a flange portion; and/or the mating connecting portion of the ring includes a curved proximal surface.

In another embodiment of the disclosure, an orthopedic fixation device for affixing the screw head of a polyaxial pedicle screw, includes a tulip defining a distal and proximal end and forming a tulip body forming an interior cavity, two opposed arms extending away from a proximal end of the body, cooperating threads disposed on mutually facing sides of each arm, and a ledge positioned at a distal end of the tulip body at an entrance to the cavity; a saddle defining a distal and proximal end, the saddle sized and dimensioned to be insertable into the tulip body, forming a U shaped groove on the saddle proximal end sized to receive a spinal fixation rod inserted between the tulip arms, forming a mating connection portion on peripheral surface of a distal end; and a ring for engaging the screw head, the ring having a first diameter smaller than the widest diameter of the screw head, formable into a second diameter larger than the widest diameter of the screw head when the screw head is passed into the ring, including a mating connection portion mateable with the mating connection portion of the saddle, whereby the ring and the saddle are mutually releaseably connectable, and positioned upon a proximal side of the tulip ledge; the screw head clampable within the tulip body interior cavity in a position between the saddle and the ring when the saddle is urged in a distal direction towards the tulip ledge.

In variations thereof, the saddle is insertable into a distal end of the tulip body; the saddle and connected ring are insertable into a distal end of the tulip body when the saddle and ring are mutually connected; and/or the tulip additionally forms a detent portion positioned distal to the threads upon an interior surface of the cavity, and the saddle forming a detent portion on a proximal end mateable with the detent portion of the tulip to mutually releaseably connect the tulip and the saddle.

In another variation thereof, the device further includes a retaining ring: positionable upon a proximal side of the tulip ledge, having a diameter larger than the diameter of the tulip ledge, and forming a ring engaging profile having a diameter smaller than a diameter of the tulip ledge; whereby the ring presses against the profile when the saddle is urged in a distal direction, to thereby prevent the ring from moving out of the cavity.

In another variation thereof, the retaining ring having a gap formed therethrough, the retaining ring thereby insertable past the tulip ledge by winding the retaining ring past the tulip ledge.

In a still further variation thereof, the ring forms a peripheral axially extending profile forming a plurality of peripheral kerfs extending partially along the length of the of the axially extending profile, forms a ramp peripherally extending radially about, and extending inwards towards, an axial center of the ring, and includes a plurality of kerfs extending through the ramp enabling the ramp to form the first and second diameter.

In other variations thereof, the ring forms one or more axially extending kerfs; the tulip includes at least one radially extending pin, the pin extending into a kerf of the ring as the ring is moved axially, the pin thereby guiding movement of the ring and blocking movement of the ring beyond an axially extending length of the kerf; and/or at least one kerf extends from a proximal surface of the ring and extends axially to a length less than an axial length of the ring, and at least one kerf extends from a distal surface of the ring and extending axially to a length less than an axial length of the ring, the ring thereby compressible about a proximal periphery and compressible about a distal periphery.

In yet further variations thereof, the ring includes a plurality of serrations on an exterior surface cooperative with an interior surface of the tulip cavity to reduce movement of the ring when a screw head is clamped; the plurality of serrations are disposed at an angle that is offset with respect to a central axis of the ring; the one or more kerfs enabling expansion of a distal peripheral end of the ring, the retaining ring including an internal profile shaped to contain the distal peripheral end of the ring and block expansion of the distal peripheral end of the ring when the distal peripheral end of the ring is seated within the internal profile; and/or the ring engaging profile is disposed distally to the tulip ledge when the retaining ring is positioned upon the tulip ledge.

In another embodiment of the disclosure, a pedicle screw comprises a head that has a rounded shape; a tool engagement disposed in an end of the head for engaging a tool for turning the screw; a shaft having a neck end and an insertion end, the head attached at the neck end; a first thread extending along at least a portion of the shaft; and a second thread extending along at least a portion of the shaft having the first thread, whereby the second thread forms a dual lead together with the first thread.

In variations thereof, the screw further includes a third thread forming a triple lead together with the first and second thread; the screw further includes a third thread and a fourth thread forming a quad lead together with the first and second thread; the minor diameter in the region of the quad lead is larger than the minor diameter in the region of only the first thread; the minor diameter in the region of both the first and second thread is larger than the minor diameter in the region of only the first thread; and/or the position of the dual lead along the shaft is determined by a position and extent of cortical bone into which the screw is to be inserted.

In other variations thereof, the position of the dual lead along the shaft is determined by a position of cortical bone of the pedicle into which the screw is to be inserted; the position of the dual lead along the shaft is determined by a position of cortical bone of the pedicle into which the screw is to be inserted, and the first thread extends along the insertion end and enters the cancellous bone of the body of the vertebra when the screw is inserted; the insertion end is pointed; the screw head is grooved; and/or the head forms a polyaxial screw head.

BRIEF DESCRIPTION OF THE DRAWINGS

A more complete understanding of the disclosure, and the attendant advantages and features thereof, will be more readily understood by reference to the following detailed description when considered in conjunction with the accompanying drawings, in which:

6

Figures 1, 2, 3, 4, 5:
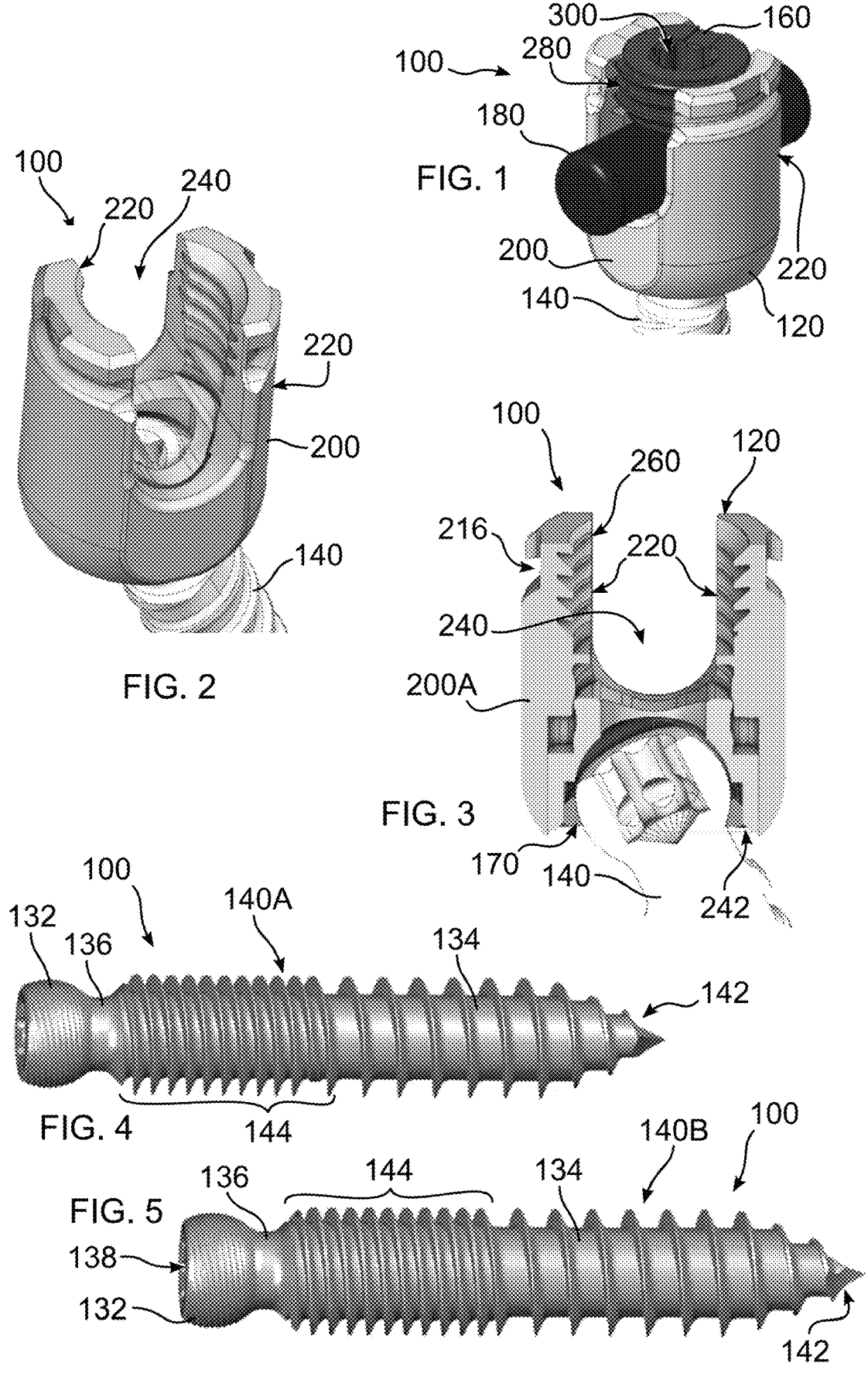

FIG. 1 depicts an orthopedic fixation device including a modular head or tulip, a bone fixation rod, a locking cap, and a modular screw, of the prior art;

FIG. 2 depicts an orthopedic fixation device in accordance with the disclosure, including a tulip, saddle, and modular screw;

FIG. 3 depicts a perspective bisected cross-sectional view of the device of FIG. 2;

Embodiment 1—Multi-Threaded Screws

Figures 5A, 6, 7, 8, 9:
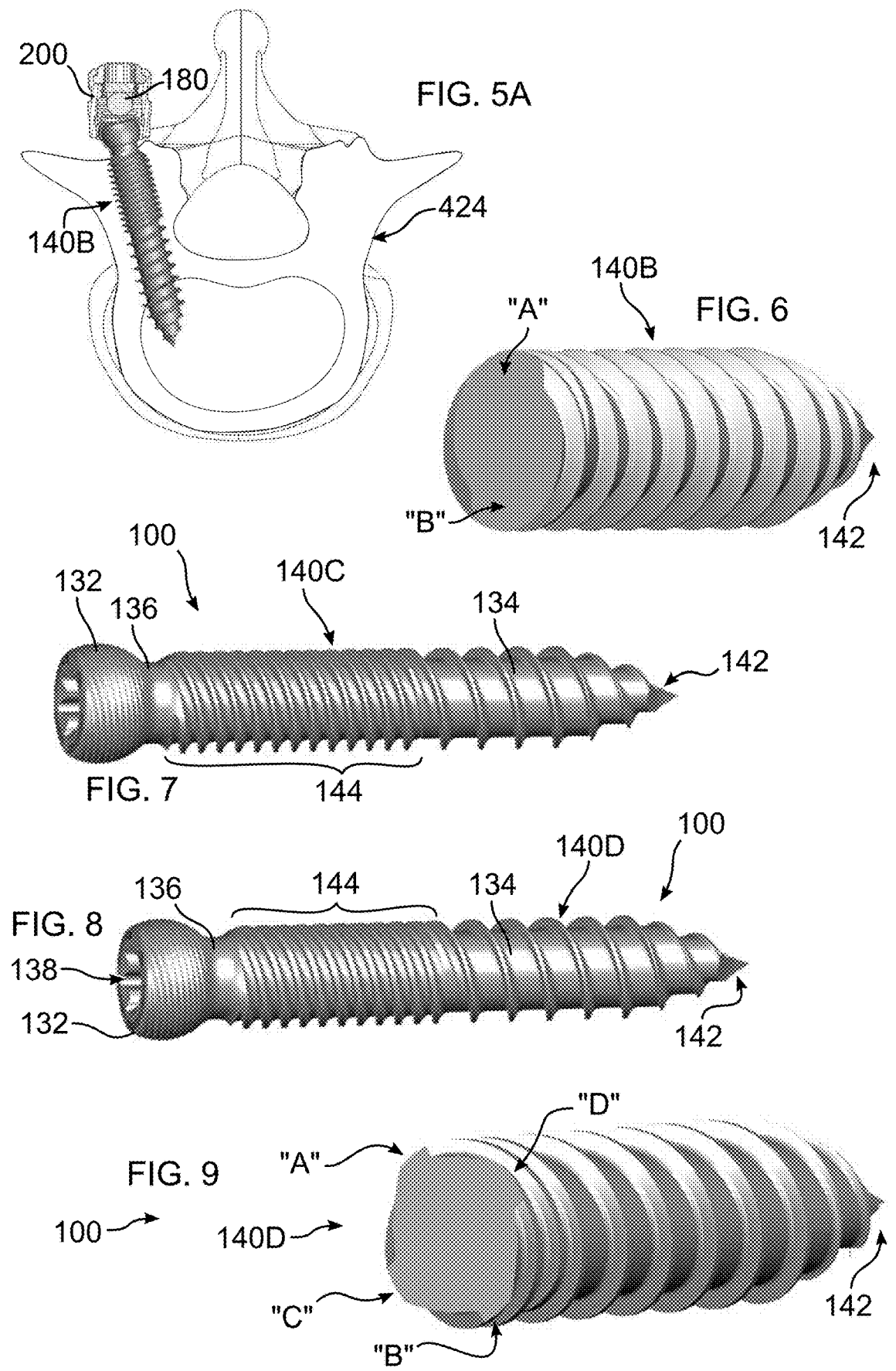

FIG. 4 depicts a polyaxial bone screw in accordance with the disclosure including multiple threads, and specifically, two threads along a portion of the screw;

FIG. 5 depicts the bone screw of FIG. 4, but with an enlarged minor diameter in the area of multiple threads;

FIG. 5A depicts a diagrammatic illustration of the bone screw of FIG. 5 deployed within a pedicle of a vertebra;

FIG. 6 depicts a cross-section through the bone screw of FIG. 4;

FIG. 7 depicts a polyaxial bone screw in accordance with the disclosure including multiple threads, and specifically, four threads along a portion of the screw;

FIG. 8 depicts the bone screw of FIG. 7, but with an enlarged minor diameter in the area of multiple threads;

FIG. 9 depicts a cross-section through the bone screw of FIG. 8;

Embodiment 2—Half-Clips

Figures 10, 10A, 11, 11A, 11B, 12, 13:
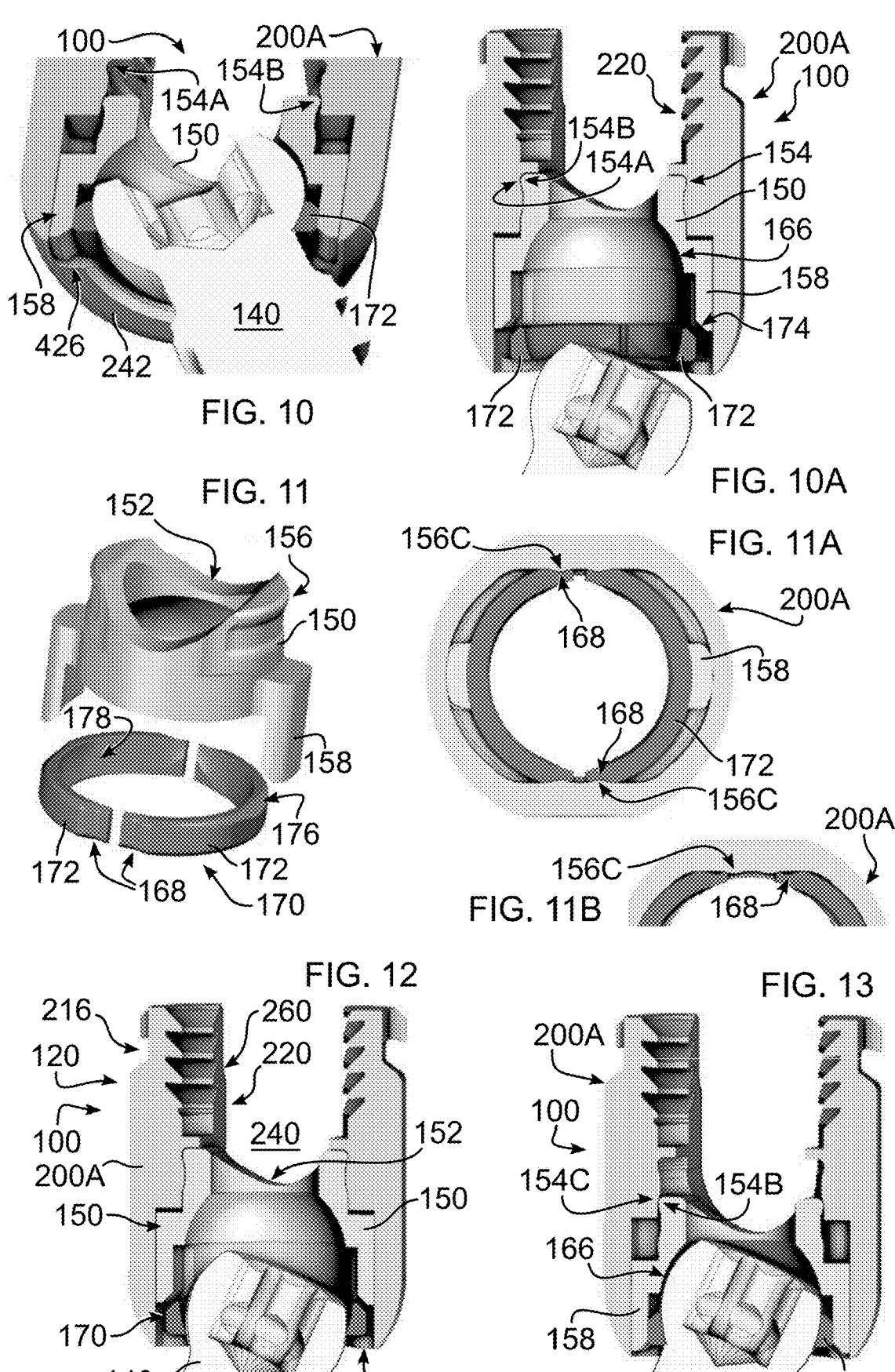

FIG. 10 depicts a bisected perspective view of an orthopedic fixation device in accordance with the disclosure, including a tulip and modular screw, and a bone screw retention system including a cooperating saddle, half-clip portions, and tulip ledge, a bone screw clamped within the tulip body interior cavity;

FIG. 10A depicts a bisected cross-sectional view of the device of FIG. 10, a bone screw being inserted into the tulip body interior;

FIG. 11 depicts a perspective view of the saddle and half-clip portions of the device of FIG. 10;

FIG. 11A depicts the detent portions and engaged with half-clips translated radially inwards, FIG. 11B depicts detent portions and engaged to retain half-clips in the radially outward position.

FIG. 12 depicts a bisected cross-sectional view of the device of FIG. 10, with a bone screw being inserted into the tulip interior;

FIG. 13 depicts a bisected cross-sectional view of the device of FIG. 10, with a bone screw being clamped between the saddle and half-clips;

Embodiment 3—Torsion Clip

Figures 14, 15, 16, 17, 18, 19:
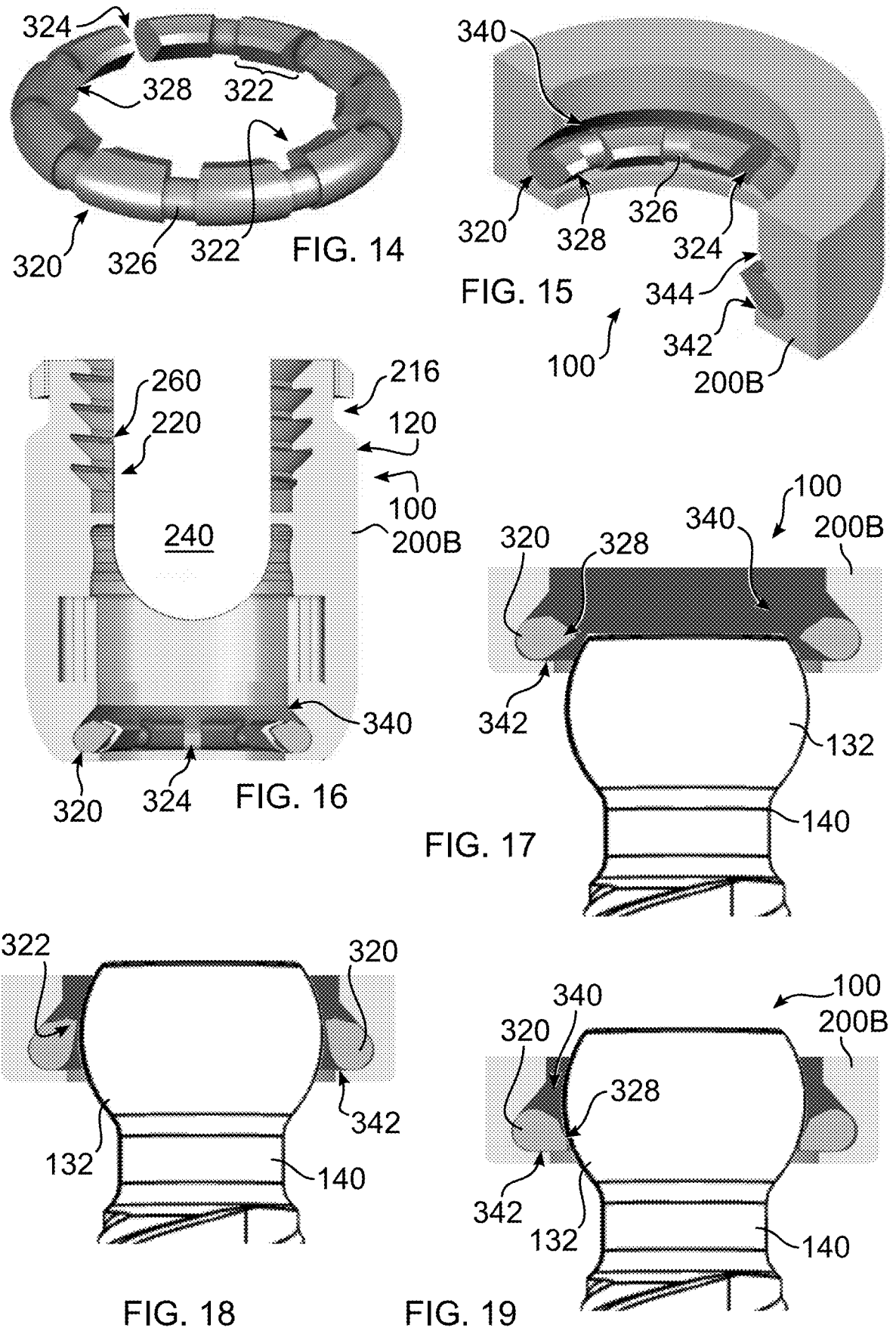

FIG. 14 depicts a torsion clip retainer in accordance with an embodiment of the disclosure;

FIG. 15 depicts a perspective bisected cross-sectional view of the torsion clip of FIG. 14, positioned within a segment of the tulip;

FIG. 16 depicts is a bisected cross-sectional view of the torsion ring of FIG. 14 assembled into a tulip in accordance with the disclosure;

FIG. 17 depicts a bone screw about to be inserted into the assembly of FIG. 16;

FIG. 18 depicts a bone screw being inserted through and twisting the torsion ring within the assembly of FIG. 16;

FIG. 19 depicts the bone screw fully inserted into the assembly of FIG. 16, the torsion ring returning to an un-twisted resting state which is blocking the exit of the bone screw;

Embodiment 4—Clipless Head

Figures 20, 21, 22, 23, 24, 25:
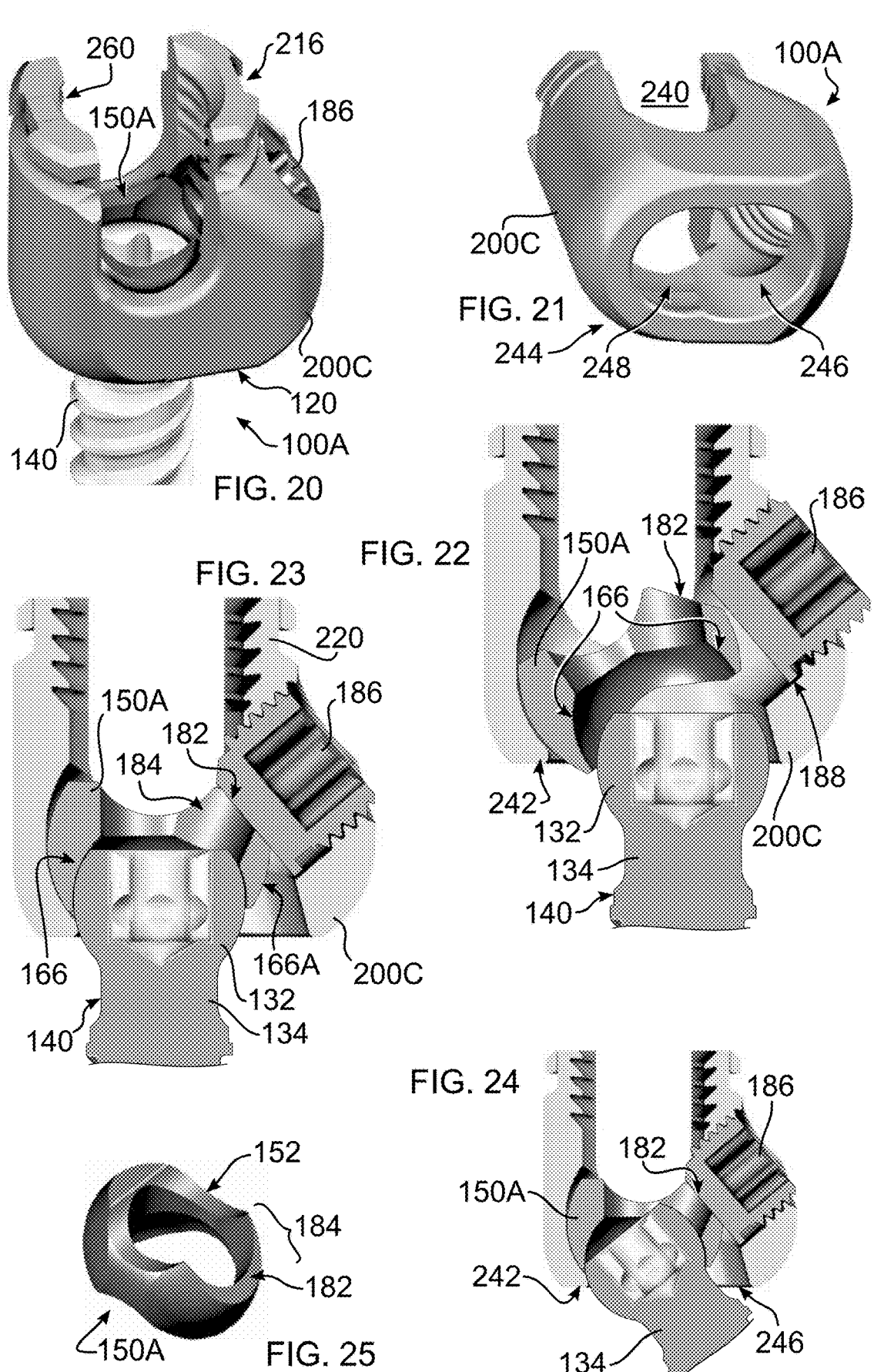

FIG. 20 depicts a perspective view of an alternative orthopedic fixation device in accordance with the disclosure, which includes an alternative saddle and tulip, the tulip having a lateral set screw;

FIG. 21 depicts a bottom view of the tulip of FIG. 20;

FIG. 22 depicts a bisected cross-sectional view of the device of FIG. 20, a bone screw being inserted;

FIG. 23 depicts a bisected cross-sectional view of the device of FIG. 20, a bone screw being clamped;

FIG. 24 depicts a bisected cross-sectional view of the device of FIG. 20, a bone screw being clamped, the screw disposed at an increased offset angle;

FIG. 25 depicts a perspective view of the saddle of FIG. 20;

Embodiment 5—Compression Clamp

Figures 26, 27, 28, 29, 30, 31, 32, 33:
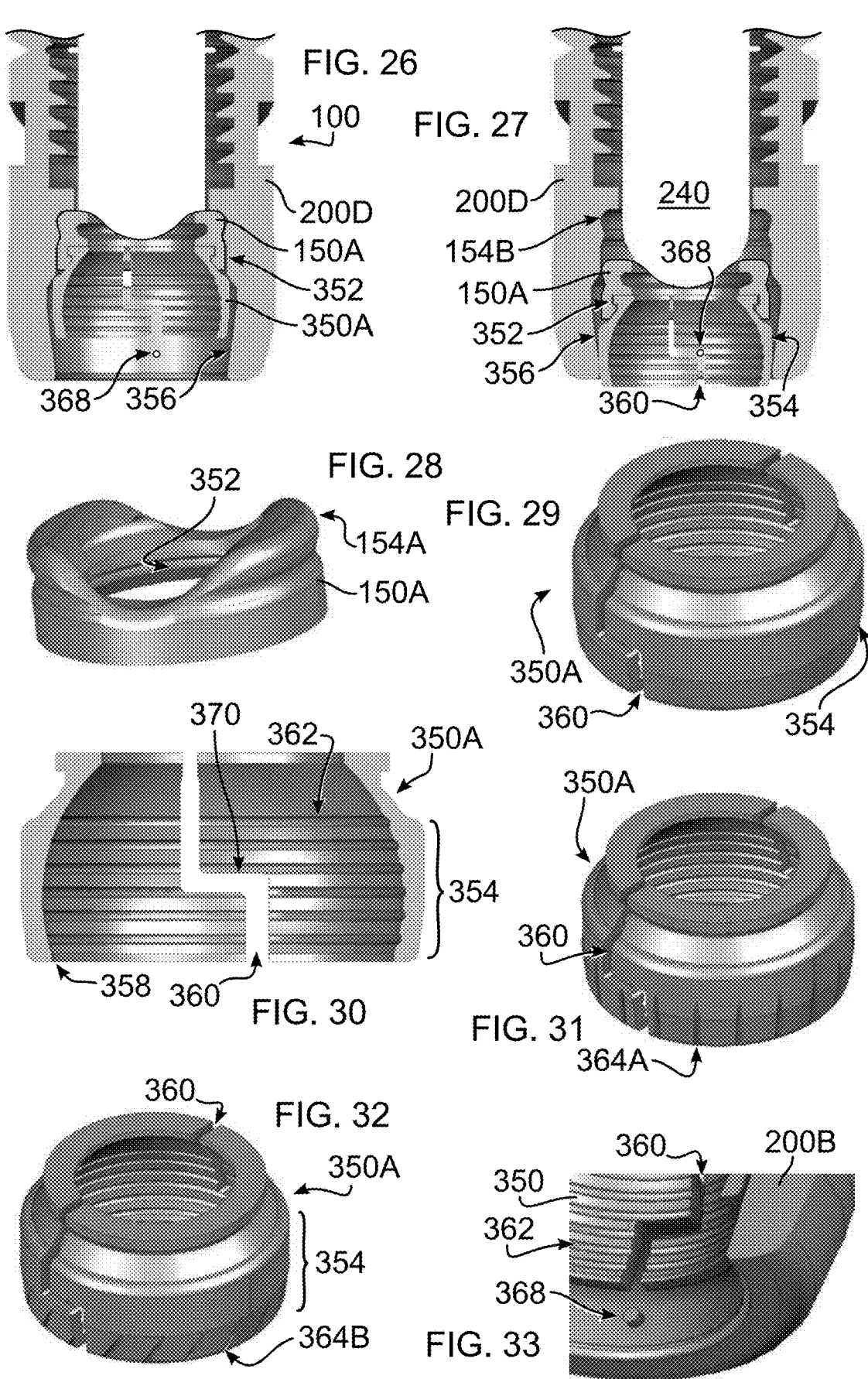

FIG. 26 depicts a bisected cross-sectional view of an alternative orthopedic fixation device in accordance with the disclosure, including an alternative tulip and saddle, the saddle clipped to a flexible compression clamp, the clamp in an uncompressed or contracted configuration;

FIG. 27 depicts the device of FIG. 26, the clamp in a compressed configuration;

FIG. 28 depicts a perspective view of the saddle of FIG. 26;

FIG. 29 depicts a perspective view of the clamp of FIG. 26;

FIG. 30 depicts an enlarged bisected cross-sectional view of the clamp of FIG. 26;

FIG. 31 depicts a perspective view of the clamp of FIG. 26 including serrations formed about an external periphery;

FIG. 32 depicts a perspective view of the clamp of FIG. 26 including serrations formed about an external periphery, the serrations formed at an angle;

Embodiment 6—Blocking Pin

FIG. 33 depicts a compression clamp and tulip in accordance with the disclosure, the tulip including a blocking pin, and the clamp including a pin guiding channel;

Embodiment 7—Clamp Kerfs

Figures 34, 35, 36, 37, 38, 38A, 39, 40, 41:
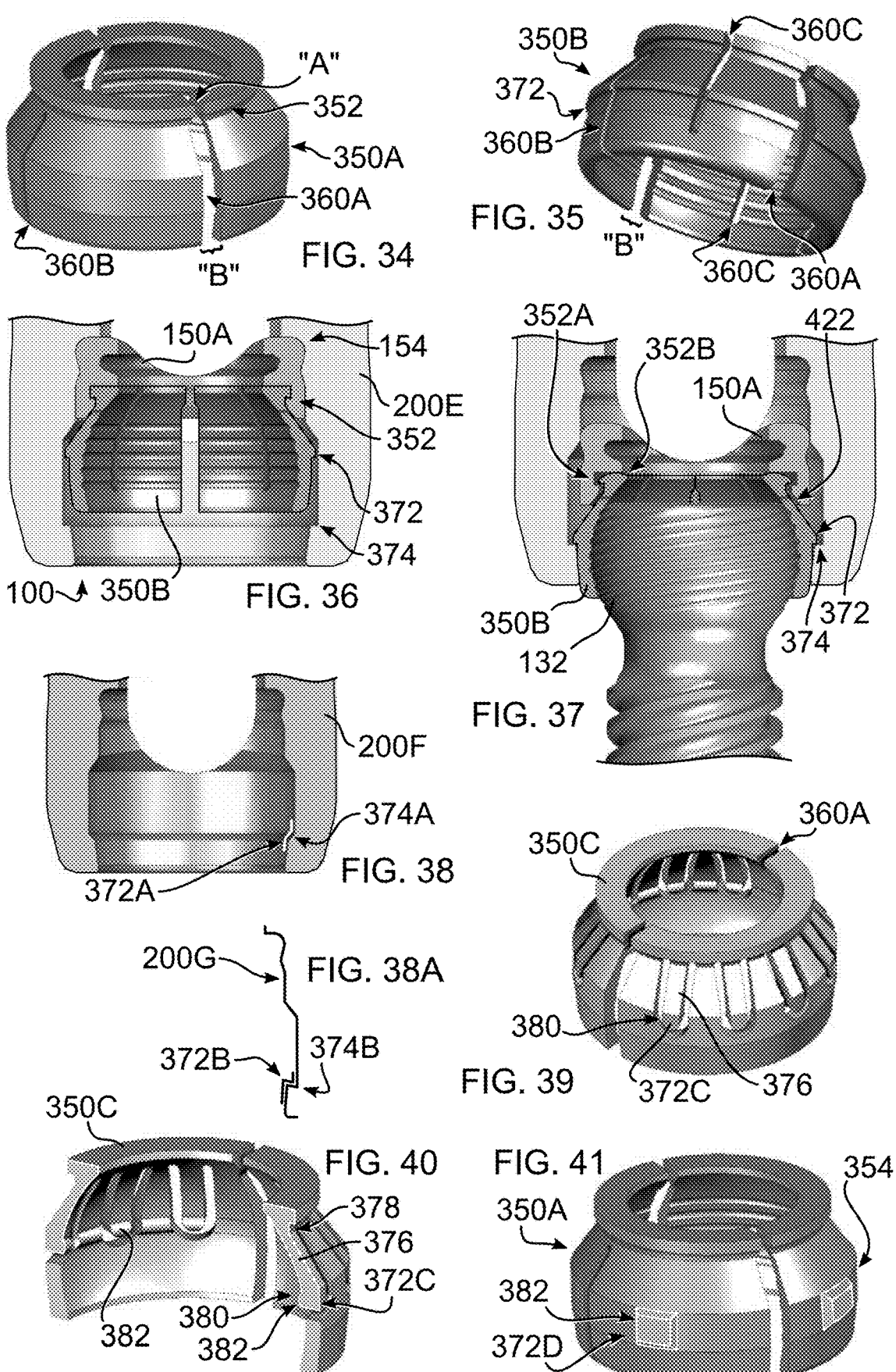

FIG. 34 depicts a compression clamp in accordance with the disclosure including segments separated by a variable width gap, and including kerfs extending from one end of the clamp and which do not separate the clamp into additional segments;

FIG. 35 depicts the clamp of FIG. 34, including additional kerfs which extend from an opposite end of the clamp, and further including a peripheral blocking flange;

Embodiment 8—Blocking Flanges

FIG. 36 depicts a bisected cross-sectional view of an orthopedic fixation device of the disclosure including the saddle of FIG. 26 attached to a clamp having segments and kerfs as in FIG. 35, and further including a blocking flange which prevents withdrawal of a clamped pedicle screw;

FIG. 37 depicts the device of FIG. 36 in a clamped and blocked position, and further depicting an alternative clip configuration between the saddle and clamp;

FIG. 38 depicts an alternative blocking shape including a compressing ramp;

FIG. 38A depicts an alternative blocking shape including a hook shape;

FIG. 39 depicts an alternative clamp of the disclosure including a plurality of flexible digits which extend to form a blocking flange when a screw head has been inserted into the clamp;

FIG. 40 depicts a bisected cross-section through the clamp of FIG. 39;

FIG. 41 depicts an alternative clamp of the disclosure including a plurality of blocking flange segments extending from an exterior surface of the clamp;

Embodiment 9—Shear Ring

FIG. 42 depicts a bisected cross-section of an alternative orthopedic fixation device of the disclosure including a clamp formed between an alternative saddle and a cooperating shear ring, retaining ring, and tulip ledge;

FIG. 43 depicts a perspective view from a lower end of the saddle of FIG. 42;

FIG. 44 depicts a perspective view of the shear ring of FIG. 42;

FIG. 45 depicts a perspective view of the retaining ring of FIG. 42;

FIG. 46 depicts a bisected cross-section through the tulip of the device of FIG. 42, with the saddle assembled and the shear ring being assembled;

FIG. 47 depicts the tulip of FIG. 46 with the shear ring and retaining ring assembled;

FIG. 48 depicts the tulip of FIG. 47 with a pedicle screw head being assembled, having broken and/or expanding a diameter of the shear ring;

FIG. 49 depicts the tulip of FIG. 48, the saddle having been pushed downwards to clamp the pedicle screw within the tulip body;

Embodiment 10—Spring Ring

Figures 50, 51, 52, 53, 54, 55, 56:
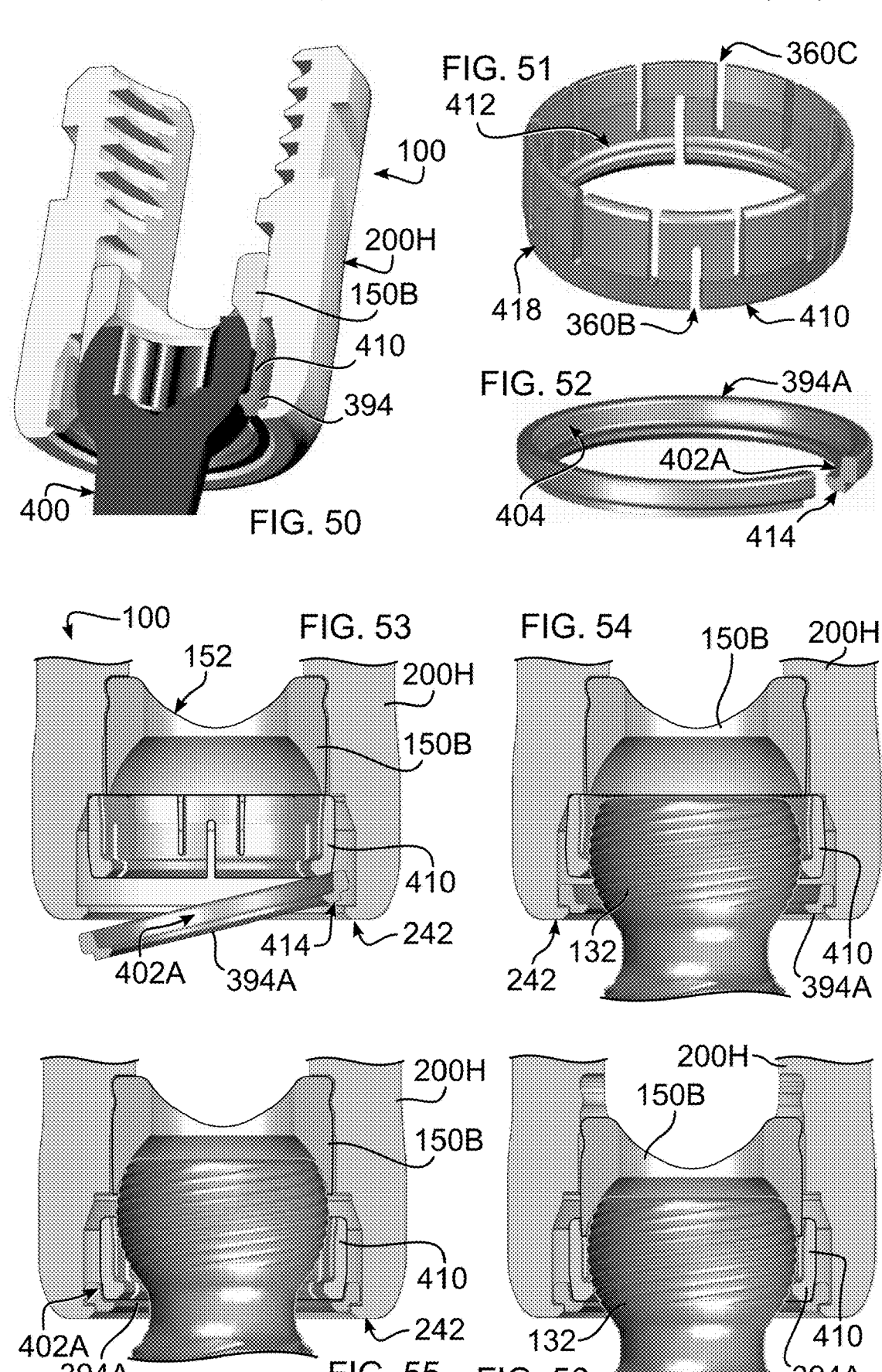

FIG. 50 depicts a bisected cross-section of an alternative orthopedic fixation device of the disclosure including the saddle of FIG. 42 and an alternative retaining clip and a spring ring substituting for the shear ring of FIG. 42, the spring ring expandable without breaking to enable a pedicle screw head to pass therethrough;

FIG. 51 depicts an enlarged perspective view of the spring ring of FIG. 50;

FIG. 52 depicts an enlarged perspective view of the retaining ring of FIG. 50;

FIG. 53 depicts a bisected cross-section through the tulip of the device of FIG. 50, with the saddle and spring ring assembled, and the retaining ring being assembled;

FIG. 54 depicts the tulip of FIG. 53 with a pedicle screw head expanding a lower diameter of the spring ring during insertion of the screw head;

FIG. 55 depicts the tulip of FIG. 54, with the screw head inserted, and the spring ring having returned to a previous diameter and dropped into the retaining ring;

FIG. 56 depicts the tulip of FIG. 55, the saddle having been pushed downwards to clamp the pedicle screw head within the tulip body;

Embodiment 11—Retained Spring Clip

Figures 57, 58, 59, 60, 61, 62, 63:
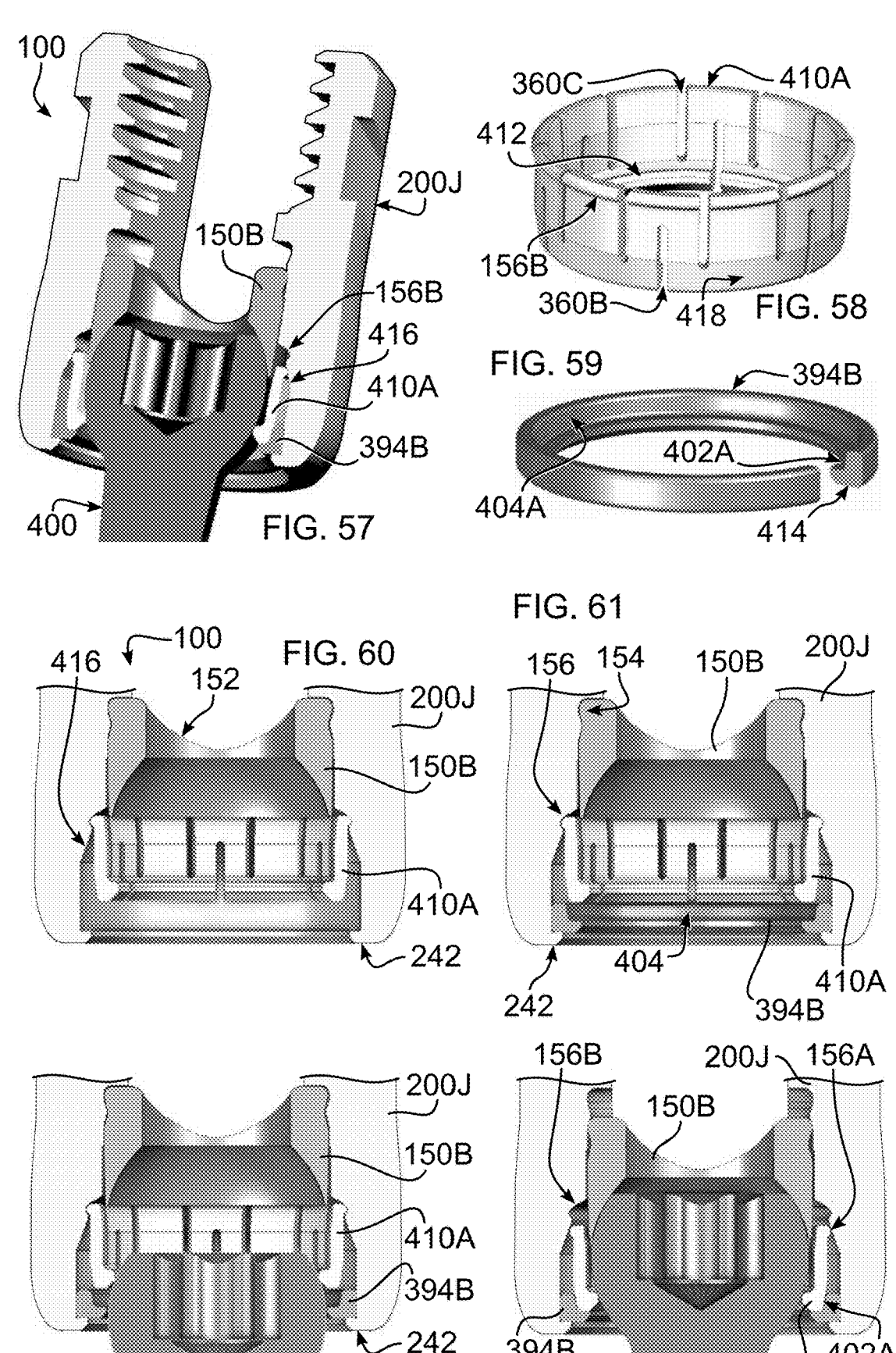

FIG. 57 depicts a bisected cross-section of an alternative orthopedic fixation device of the disclosure including the saddle of FIG. 42 and an alternative retaining clip and a spring ring substituting for the shear ring of FIG. 42, the spring ring expandable without breaking to enable a pedicle screw head to pass therethrough, the spring ring connectable to the saddle;

FIG. 58 depicts an enlarged perspective view of the spring ring of FIG. 57;

FIG. 59 depicts an enlarged perspective view of the retaining ring of FIG. 57;

FIG. 60 depicts a bisected cross-section through the tulip of the device of FIG. 57, with the saddle and spring ring connected by a clip connection and assembled into the tulip;

FIG. 61 depicts the tulip of FIG. 60 with the retaining ring assembled;

FIG. 62 depicts the tulip of FIG. 61, with the screw head being inserted and expanding the spring ring lower diameter;

FIG. 63 depicts the tulip of FIG. 62, the saddle and connected spring ring having been pushed downwards to clamp the pedicle screw head within the tulip body;

Embodiment 12—Locking Clamp

Figures 64, 65, 66, 67, 68, 69, 70:
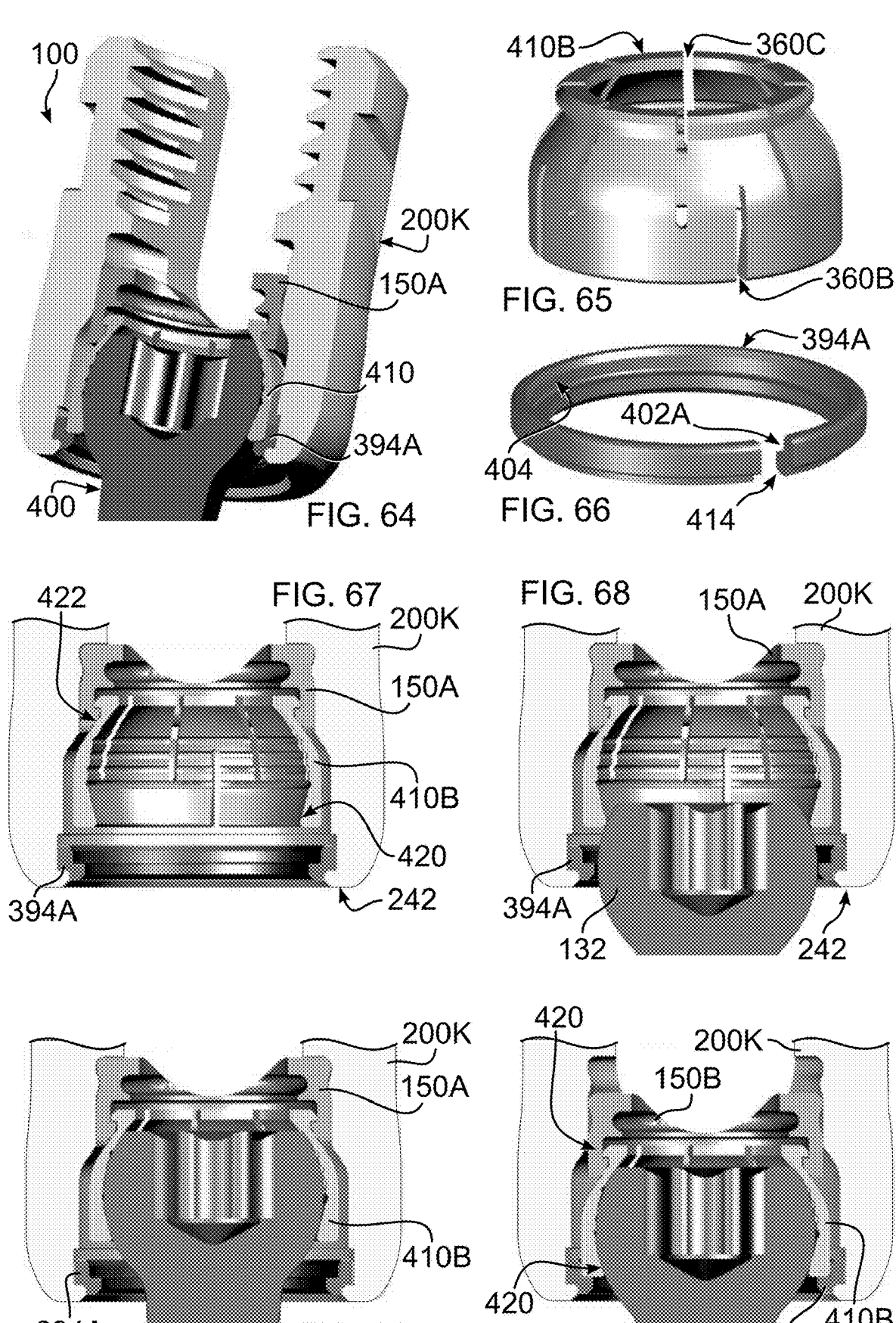

FIG. 64 depicts a bisected cross-section of an alternative orthopedic fixation device of the disclosure including a saddle similar to that of FIG. 26, but with an alternative engagement ramp profile, an alternative retaining clip, and an expandable spring ring connectable to the saddle, the spring ring containing a shaped lower profile;

FIG. 65 depicts an enlarged perspective view of the spring ring of FIG. 64;

FIG. 66 depicts an enlarged perspective view of the retaining ring of FIG. 64;

FIG. 67 depicts a bisected cross-section through the tulip of the device of FIG. 64, with the saddle and spring ring connected by a clip connection, the clipped combination and retaining ring assembled into the tulip;

FIG. 68 depicts the tulip of FIG. 67 with the pedicle screw head contacting the shaped profile of the spring ring to thereby expand a lower diameter of the spring ring for assembly of the screw head;

FIG. 69 depicts the tulip of FIG. 68, with the screw head positioned within the spring ring, the spring ring resuming a reduced diameter to conform to the spherical shape of the pedicle screw head; and FIG. 70 depicts the tulip of FIG. 69, the saddle and connected spring ring having been pushed downwards to engage the shaped profile of the spring ring with the retaining ring to thereby clamp the pedicle screw head within the tulip body.

DETAILED DESCRIPTION OF THE DISCLOSURE

This written description uses examples to disclose the embodiments, including the best mode, and also to enable those of ordinary skill in the art to make and use the invention. The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

Note that not all of the activities described above in the general description or the examples are required, that a portion of a specific activity may not be required, and that one or more further activities can be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

It can be advantageous to set forth definitions of certain words and phrases used throughout this patent document. The term "communicate," as well as derivatives thereof, encompasses both direct and indirect communication. The term "discreet," as well as derivatives thereof, references to the amount of skin exposed by a user of the garment, rather than the type of style of the garment. The terms "include" and "comprise," as well as derivatives thereof, mean inclusion without limitation. The term "or" is inclusive, meaning and/or. The phrase "associated with," as well as derivatives thereof, can mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items can be used, and only one item in the list can be needed. For example, "at least one of: A, B, and C" includes any of the following combinations: A, B, C, A and B, A and C, B and C, and A and B and C.

Also, the use of "a" or "an" are employed to describe elements and components described herein. This is done merely for convenience and to give a general sense of the scope of the invention. This description should be read to include one or at least one and the singular also includes the plural unless it is obvious that it is meant otherwise.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function.

Benefits, other advantages, and solutions to problems have been described above with regard to specific embodiments. However, the benefits, advantages, solutions to problems, and any feature(s) that can cause any benefit, advantage, or solution to occur or become more pronounced are not to be construed as a critical, required, sacrosanct or an essential feature of any or all the claims.

After reading the specification, skilled artisans will appreciate that certain features are, for clarity, described herein in the context of separate embodiments, can also be provided in combination in a single embodiment. Conversely, various features that are, for brevity, described in the context of a single embodiment, can also be provided separately or in any subcombination. Further, references to values stated in ranges include each and every value within that range.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

Headings are provided for the convenience of the reader, and are not intended to be limiting in any way.

Additional aspects, advantages and/or other features of example embodiments of the invention will become apparent in view of the following detailed description. It should be apparent to those skilled in the art that the described embodiments provided herein are merely exemplary and illustrative and not limiting. Numerous embodiments or modifications thereof are contemplated as falling within the scope of this disclosure and equivalents thereto.

Embodiments of the disclosure are generally directed to orthopedic implants, assemblies, systems, instruments, and methods. Specifically, embodiments are directed to modular bone fastener assemblies configured to secure one or more spinal rods, installation instruments, and navigation methods. The modular bone fastener may include a modular screw configured to be inserted into bone with or without navigation and/or robotic assistance. One or more screw extender instruments may provide for secure attachment to and improved maneuverability of the modular screw. After screw installation, a modular head may be deployed and attached to the modular screw with or without navigation and/or robotic assistance. Navigational tracking of the procedure and/or a robotic system may be provided, for example, for accurate placement of the modular screw and/or tulip head, tracking of the vertebral bodies, assembly of the modular head onto the modular screw, and/or intraoperative feedback. These implants and instruments may be used in open and percutaneous approaches to the posterior spine with or without assistance of a navigation or robotic system. Although generally described with reference to the spine, it will be appreciated that the devices and systems described herein may be applied to other orthopedic locations in the body and other medical applications, such as trauma.

Overview

Referring now to FIGS. 1-3, an orthopedic fixation device, implant, or bone stabilizing assembly 100 is shown according to one embodiment. The implant or bone stabilizing assembly 100 may include a tulip head or modular head 120, a bone fastener or modular screw 140, and a locking cap 160 (FIG. 1) for securing a spinal rod 180 in the modular head 120. In the case of a polyaxial assembly 100, tightening the locking cap 160 compresses the rod 180 into the tulip head 120, thereby restricting motion of the modular screw 140 and forming a rigid construct with the bone fastener at a desired angle. The modular screw 140 may be deployed independently from the modular head 120. For example, the modular screw 140 may be first installed in bone and the modular head 120 may be later deployed and assembled onto the modular screw 140 during the surgical procedure. Alternatively, the modular head 120 and screw 140 may be pre-assembled prior to installation.

The tulip head 120 includes a body 200 and arms 220 that extend upwardly from the body 200. A central bore 240 may extend through the tulip head 120 The opposed arms 220 may define a U-shaped channel, transverse to the bore 240, sized and configured to accept the rod 180. Each of the arms 220 has an interior surface defining a threaded portion 260 for engaging the threaded locking cap 160. The outer surface of the tulip head 120 may define one or more tool engagement 216, such as the groove shown, for holding and maneuvering the tulip head 120 with a suitable tool.

Rod 180 may be secured in the tulip head 120 with locking cap 160. Locking cap 160 may define an outer threaded portion 280 configured to interface with the inner threaded portion 260 of the tulip head 120 The locking cap 160 may be in the form of a set screw with a drive recess 300 configured to be engaged by a driving instrument, which is able to insert and tighten the locking cap 160 in the tulip head 120. The bottom of locking cap 160 may be flat or otherwise configured to ensure consistent contact with rod 180.

EMBODIMENT 1—MULTI-THREADED SCREWS

Turning now to FIGS. 4-5, bone fastener 140 may include a bone screw, anchor, clamp, or the like configured to engage bone. In the embodiment shown, bone fastener 140 is a modular bone screw 140, such as a pedicle screw. The modular screw 140 extends from a proximal end with a screw head 132 to a distal end configured to engage bone. The modular screw 140 has a threaded shaft 134 connected to the screw head 132 by a neck portion 136. It will be appreciated that the threaded shaft 134 may have a number of different features, such as lead(s), thread pitch, thread angle, shaft diameter to thread diameter, overall shaft shape, and the like, depending, for example, on the particular application, and as detailed herein. The assembly 100 of the disclosure can be used with a wide variety of such fasteners 140 as are previously known, hereafter developed, and as detailed in accordance with this disclosure.

Threaded shaft 134 may terminate at a tip 142 at the distal end, which may be blunt, pointed, or otherwise configured to engage bone. While the screw head 132 may have any general shape, in the case of a polyaxial fastener, at least a portion of the screw head 132 may have a curved or rounded surface in order to allow for rotational movement and/or angular adjustment of the bone fastener 140 with respect to a clamp within the tulip head 120, for example as detailed herein, or as known in the art. For example, at least a portion of the screw head 132 may be shaped to form a portion of a ball or a sphere, for example as illustrated. The spherical screw head 132 may define one or more drive and/or engagement 138 in the head 132, such as the surfaces shown, for example, that can be engaged by a screw-driving instrument or other device to turn the screw and drive the screw into body tissue. In one embodiment, the bone screw head 132 defines a hexalobular drive recess 38 for driving the screw 140 into bone. It will be appreciated that any suitably shaped tool drive engagement 138 may be provided. The screw head 132 can include grooves to improve grip during compression of the screw head within the tulip.

With further reference to FIGS. 4-9, bone screws 140 include variations 140A-140D which have multiple lead threads. In FIGS. 4-6, bone screws 140A and 140B are threaded screws where the number of threads double towards the proximal/head 132 end of the pedicle screw, forming a 'dual lead', 'two start', or 'double thread' screw. A first thread begins near the distal end, and a second thread, begins at a distance away from the distal end, and can have a start 180 degrees offset from the start of the first thread. Both the first and second threads continue together to terminate near neck 136.

FIG. 5A diagrammatically illustrates bone screw 140B in a position within a vertebra 424, showing the multithreaded portion 144 located within cortical bone of the pedicle. It should be understood that multithreaded portion 144 as illustrated is sized to optimize deployment within the pedicle, however depending upon various anatomy within which bone screws of the disclosure may be used, which include bones other than vertebrae, multithreaded portion 144 may extend over other portions of the screw, or extend along the entire length of the screw.

FIGS. 7-8 are similar to FIGS. 4-5, except that a quad lead thread is started after an initial length of dual lead thread. Cross-sections after the start of multiple threads are shown in FIGS. 6 and 9, reflecting the embodiments of FIGS. 5 and 8, respectively. Two threads A and B are visible in FIG. 6, and four threads A-D are visible in FIG. 9. Providing multiple threads positions more threads within the most sturdy and high density bone structure, improving engagement, and resulting in increasing strength and resistance to toggling and pull-out. It should be understood that a triple threaded shaft can be formed in a like manner, or other multiple lead threads.

FIGS. 5 and 8 have a minor diameter (at base of the threads) in the multithreaded region that is larger than the minor diameter in the single threaded region, which the inventors have found increases the pullout/toggle strength. In FIGS. 4 and 7, the minor diameter remains the same throughout both the single and multithreaded regions.

As the pitch throughout the single and double threaded regions are a ratio of each other, the entire threaded region advances into the body at the same rate, as screw 140 is turned. With multiple threads, the rate of insertion increases with additional threads, as the lead increases with each additional thread. For example, the dual threaded embodiment of FIGS. 4-5 will be inserted with half as many turns as a single threaded screw, and the quad threaded embodiment of FIGS. 7-8 will be inserted with one quarter as many turns as a single threaded screw.

The multi-threaded region 144 is sized and located along shaft 134 in order to correspond to an anticipated extent of cortical bone where screw 140A/B/C/D is to be installed/implanted. The single threaded region is provided to facilitate insertion and/or to be disposed within more fragile cancellous bone once installed.

Embodiment 2—Half-Clips

With further reference to FIG. 3, and additional reference to FIGS. 10-13, a bone stabilizing assembly 100 of the disclosure enables assembly of a screw 140 either before or after the screw has been installed. More particularly, screw 140 is retained when the saddle 150 is deployed to a down position interlocking saddle 150 and clip 170, and is further clamped when locking cap 160 is tightened. Clip 170 is formed as two half-clips 172. A distal ledge 242 retains clip 170 axially within tulip body 200A, while half-clips 172 are each movable to translate radially towards an axial centerline of tulip body 200A to form a contracted diameter and away from an axial centerline to form an expanded diameter. When saddle 150 is in the position shown in FIGS. 10 and 13, a contracted diameter is formed. In this manner, as head 132 is pushed between half-clips 172 in FIG. 11, half-clips 172 are forced apart by head 132 to form the expanded diameter, each half-clip 172 moving radially away from the axial centerline sufficiently to allow the widest portion of head 132 to pass into tulip body 200A.

A spinal fixation rod 180 is placed into tulip bore 240 to rest within a rod-shaped portion 152 of saddle 150, which provides consistent deformation and frictional contact with the rod for locking. Saddle 150 is disposed within an elliptical recess which aligns saddle 150 to receive the rod, and which prevents rotation of saddle 150. Locking cap 160 is then threaded along arms 220 to drive rod 180 into portion 152 to thereby drive saddle 150 downwards towards the body into a locked position, as shown in FIG. 13. After all components thus connected are positioned as therapeutically needed, cap 160 is securely tightened to thereafter retain a mutual relationship of the components.

More particularly, saddle 150 can be maintained in an unlocked position, as shown in FIGS. 10A and 12, by a detent 154 formed by saddle detent portion 154B in saddle 150 and a mating tulip detent portion 154A formed in tulip body 200. Detent 154 is formed about part or all of a periphery of the saddle and tulip body. In the figures, detent 154B (FIG. 10/10A) is formed as a protrusion of saddle 150 and tulip detent 154A as a recess, although these elements can be reversed, or another form of detent can be provided, for example a spring loaded ball or other movable part, as is known.

In an embodiment, detent 154 can provide an additional feature of maintaining a desired position of tulip body 200 once manually adjusted, for example to facilitate assembly of components into the tulip intraoperatively. More particularly, with reference to FIGS. 10 and 13 as examples, a detent slope 154C is provided below tulip detent portion 154A, which cooperates with saddle detent portion 154B to compressively interfere with saddle detent portion 154B to urge saddle detent portion 154B downwards (as viewed) towards a locking position of saddle 150 and fastener 140. An extent of force exerted and thus a stiffness of a connection between tulip body 200 and fastener 140 can be adjusted based upon an extent of interference between slope 154C and saddle detent portion 154B, and the angle of slope 154C, each of which can be chosen to achieve stability of tulip body 200 in engagement with fastener 140, while allowing for ready manual movement of tulip body 200. This feature can be provided with other embodiments with detents described herein.

Saddle 150 is provided with locking prongs 158 which move to a position interposed between half-clips 172 and the tulip body when saddle 150 is moved to the locked position. As can be seen in FIG. 10, in particular, prongs 158 can stop at ledge 242, or as shown descend distally through a gap 426 in ledge 242. Mating ramps or chamfers 174 and 176 on locking prongs 158 and half-clips 172, respectively, guide the half-clips to translate radially inwards towards the central axis of tulip body 200, to block screw head 132 from leaving tulip body 200. Prongs 158 remain between half-clips 172 and tulip body 200A when in the locked position, to prevent screw head 132 from being released.

Half-clips 172 are each provided with an inner screw head contacting surface 178 which is shaped to mate with screw head 132 to increase a contact area therebetween. For the same reason, a screw head contacting portion 166 of saddle 150 is shaped to mate with screw head 132.

With reference to FIGS. 11A-11B, which is a cross-section through half-clips 172, it may be seen that half-clips 172 are each provided with two opposed detent portions 168 which each mate with a detent portion 156C of tulip body 200A, which detent portions cooperate to retain each half-clip in a radially outwards position to facilitate entry of screw head 132. These mating surfaces further ensure an alignment of chamfers 174 and 176 as half-clips 172 trans-late radially inwards. FIG. 11A depicts the detent portions 156C and 168 engaged with half-clips 172 translated radi-ally inwards, blocking exit of screw head 132. FIG. 11B depicts detent portions 156C and 168 engaged to retain half-clips in the radially outward position.

To release screw head 132, saddle 150 is pushed or pulled away from screw head 150, for example using a suitable tool, to allow half-clips 172 to once again translate perpen-dicularly with respect to the central axis, moving out of contact with screw head 132 and forming an expanded diameter allowing sufficient clearance for the widest portion of screw head 132 to pass out of tulip body 200A.

Embodiment 3—Torsion Clip

With reference to FIGS. 14-19, in an embodiment of the disclosure, a torsion ring 320 is provided with a peripheral cam surface 328 disposed upon cam lobe segments 322, and a division 324 through the ring at a peripheral location. Ring 320 is disposed within a ring shaped chamber 340 positioned within tulip body 200B at a distal or bottom end (as viewed) thereof. Chamber 340 is isolated and enlarged in FIG. 15 for clarity, in which it may be seen that chamber 340 is likewise provided with a cam surface 342. A chamfer 344 is provided within an upper portion of chamber 340 to provide relief space for movement of cams lobe segments 322. Ring 320 can be made of any biocompatible material of sufficient strength, flexibility, and durability, and which has a high elasticity. Examples include titanium or nitinol.

Division 324 of ring 320 can be provided to facilitate insertion of ring 320 into tulip body 200B. More particu-larly, one end of ring 320 at division 324 can be passed into the interior cavity of tulip body 200B, and the remainder of ring 320 can subsequently be threaded/wound into the interior.

In use, tulip body 200B is pressed onto head 132 of screw 140 before or after screw 140 is installed within the body (FIG. 17). As tulip body 200B and head 132 are joined, screw head 132 contacts a distal or lower side (as viewed) of cam 328 causing distortion of torsion ring 320 due to pressure from head 132 (FIG. 18). The distortion can have the form of torsional flexing or twisting. Insertion of head 132 through ring 320 can be facilitated by the narrowed diameter 326 adjacent to cam 328, and the flexibility of the materials chosen for ring 320.

After screw 140 has been inserted into tulip body 200B, ring 320 can resume the ring resting shape as shown in FIG. 17 prior to screw head 132 insertion. In an embodiment, the resting state (FIG. 17) is approximately halfway between up (FIG. 18) and down (FIG. 19) positions to minimize defor-mation of ring 320 from its neutral state and to minimize stresses. Further, the resting state provides a slanted contact surface which is more easily pushed aside as screw head 132 is inserted. Screw head 132 can then become secured in a desired position as described with respect to Embodiment 1, above, with the exception that locking prongs 158 are not needed.

More particularly, as saddle 150 is urged against head 132 by rotation of cap 160, head 132 will eventually exert pressure against an upper surface of cam 328, in an opposite direction of movement relative to insertion. As can be seen in FIG. 19, when cam 328 rest against chamber cam surface 342, ring 320 is twisted in a reversed or opposite direction with respect to twisting during insertion, until cams 328 contact chamber cam surface 342, whereby cams 328 are pinched between head 132 and cam surface 342, and no further twisting of torsion ring 320 is possible. As such, screw head 132 is prevented from moving any further in a direction out of tulip body 200B.

Removal can be accomplished by unscrewing screw 140, by inserting sleeve segments of a tool between screw head 132 and cam lobe segments 322, or by using a suitable tool to pull tulip body 200B relative to head 132 with sufficient force to overcome a force imparted by ring 320 and chamber cam surface 132.

Cams 328 are shown separated into cam lobe segments 322 to provide additional flexibility. In an embodiment, cams 328 are disposed upon a continuously formed periph-eral cam lobe that has the same cross-sectional shape as cam lobe segments 322 and which functions in the same manner, but is not divided into separated cam lobe segments by narrowed diameters 326.

Embodiment 4—Clipless Head

With reference to FIGS. 20-25, bone stabilizing assembly 100A includes a tulip body 200C which includes a bottom (as viewed) or distal end 244 with two intersecting openings. With reference in particular to FIG. 21, a first opening 246 is large enough for screw head 132 to pass into tulip body 200C, and a second opening 248 is large enough for screw shaft 134 to pass, and to toggle at various angles, but which is too small for screw head 132 to pass. The intersection between the first and second openings is large enough to enable passage of screw shaft 134 therebetween.

In this manner, screw 140 can be loaded into tulip body 200C, before or after screw 140 is installed in the body, by passing screw head 132 into first opening 246, and trans-lating screw 140 laterally to position screw head above second opening 248. Screw head 132 can thereafter be prevented from again moving laterally over first opening 246 by being blocked, thereby locking screw head 132 within tulip body 200C. Blocking is carried out by a saddle 150A (FIG. 25) which includes a lateral clamping face 182 positioned on a lateral extension 184, which cooperates with a set screw 186 threadably retained in tulip body 200C.

In FIG. 22, saddle 150A is rotated to align screw head contacting portion 166 of saddle 150A with lateral portion 166A pivoted away from first opening 246. This forms an expanded diameter of saddle 150A which admits passage of screw head 132. This can be accomplished by pushing screw head 132 against saddle 150A during insertion, or position-ing saddle 150A in advance. As screw 140 is translated laterally, screw 140 pushes against the screw head contact-ing portion 166 to cause lateral portion 166A to rotate downwards towards first opening 246 to form a contracted diameter, and to cause screw head 132 to become fully seated within saddle 150A. In this manner, saddle 150A includes both a rod saddle and a ring 248 having an expanded and contracted diameter depending on a rotational position thereof Additionally, screw head 132 contacts tulip ledge 242, which has a peripheral diameter at opening 248 that is smaller than screw head 132. This results in saddle clamping face 182 becoming aligned for contact with laterally approaching set screw 186. As set screw 186 is tightened, saddle 150 urges screw head 132 against ledge 242 to lock spherical ball joint motion of screw head 132 within tulip body 200, while also blocking translation of screw head 132 laterally towards opening 246. Subsequently, as detailed elsewhere herein, as cap 160 is threaded to push rod 180 into saddle 150A, screw head 132 is further urged against ledge 242 to further secure an orientation of screw head 132.

The set screw is positioned at an angle with respect to a central axis of the tulip central bore 240 (the rod slot) to avoid central bore 240 and locking cap threads 260, and to allow the medical practitioner to drive set screw 186 through a working corridor available in open surgical procedures. A set screw flange 188 prevents accidental disassembly of set screw 186 from tulip 150A.

It should be understood that the aforedescribed features enable bottom-loading of screw 140 (a) after installation of screw 140 within the body, or (b) before installation of screw 140 within the body, whereby a screw 140 is loaded through bore 240 and is then installed within bone, after which screw head 132 is secured within tulip body 200 as described above.

As shown in FIG. 24, first opening 246 provides relief for disposing screw 140 at a greater angle (hypermobility) with respect to an axis through bore 240 than would be possible with other designs. More particularly, screw shaft 134 can pass through the area of opening 246 which would otherwise be blocked by ledge 242. Accordingly, tulip body 200C can be positioned to exploit this feature where therapeutically beneficial.

Bone stabilizing assembly 100A enables separation of screw 140 and tulip body 200C by loosening set screw 186 and translating screw 140 laterally to opening 246. Additionally, screw 140 can be affixed in position by either set screw 186 or locking cap 160, or both.

Embodiment 5—Compression Clamp

With reference to FIGS. 26-44, compression clamps 350 cooperate with saddle 150A to provide a controlled clamping of screw 140. Clamps 350 provide alternatives to the fixation devices. Such clamps improve the locking efficiency and strength of an orthopedic fixation device, particularly in terms of head pull-off and stiffness of a modular or preassembled screw and shank assembly. A specific and known amount of torque can be applied to the locking cap to reliably lock a position of all aspects of the tulip and rod interconnection. The locking cap torque is the only energy that is required to cause this locking.

If an excess amount of torque is applied to cap 160, the tulip arms 220 can become distorted or splayed, which can result in suboptimal performance. Locking cap efficiency can be increased but splay can also increase as load is transferred radially into the threads 260. Where clamping efficiency is improved, lower torque can be applied to the locking cap, and forces which could give rise to distortion are reduced. Clamps 350 enable application of a reduced locking cap torque while maintaining or improving rod and screw head clamping strength.

In FIGS. 26-27, a saddle 150A forms a detent engagement with tulip body 200D, in a manner similar to that of FIGS. 12-13. However, a separate compression clamp 350A is movably attached to saddle 150A by a dovetail or tongue and groove connection formed between saddle 150A and clamp 350A, as detailed in the cited reference. A screw head 132 is inserted into clamp 350A when the clamp is in the up/disengaged/release position shown in FIG. 26. Clamp 350A forms an expanded diameter due to expansion of kerf 360 to enable screw head 132 to pass into clamp 350A. Clamp 350A moves to a down/engaged/clamped position through force imparted by locking cap 160 which bears upon rod 180 which in turn bears upon saddle 150A (to overcome the resistive force of detent 154), which in turn bears upon clamp 350A through saddle/clamp clip connection 352 which in the embodiment shown forms a tongue and groove connection.

As clamp 350A is moved to the clamped position, external peripheral ramp 354 of clamp 350A slides along internal peripheral ramp 356 of tulip 200D. Tulip ramp 356 forms a decreasing diameter in the direction of downward movement of clamp 350A, thereby pressing clamp ramp 354 inwards towards a central axis of clamp 350A, thereby causing a diminution or contraction of the diameter of clamp 350A, resulting in compression and fixation of screw head 132. The diameter of clamp 350A can be reduced due to kerf 360, which provides room for inwards movement of portions of clamp 350A.

More particularly, with reference to FIGS. 29-30, clamping strength and reliability are improved at least by the following modifications; an internal radius of clamp 350A is extended at a lower periphery 358 to extend further under screw head 132; the width of kerf split 360, and the diameter of internal grooves 362, are reduced, resulting in greater contact with screw head 132; and external peripheral ramp 354 is elongated, resulting in a greater contact area with tulip internal peripheral ramp 356.

Referring now to FIG. 31, clamp 350B can include serrations 364 on an external surface engaged with tulip body 200, for example spaced serrations 364A peripherally disposed about external peripheral ramp 354, which reduce sliding friction between external peripheral ramp 354 clamp 350 and tulip internal peripheral ramp 356. Other orientations of serrations 364 can be provided, for example serrations 364B as shown upon example clamp 350A in FIG. 32, which are skewed from vertical. Serrations 364A-B are shown at a lower peripheral edge of clamp 350A, however they may be placed at other locations along external peripheral ramp 354. In addition or alternatively, serrations 360 may be formed on tulip internal peripheral ramp 356. Serrations 364 may work by forming a shallow piercing of a mating surface to thereby increase sliding friction between the mating surfaces.

Embodiment 6—Blocking Pin

With reference to FIGS. 26-27 and 33, a pin 368 can be fastened to and extend from an internal surface of tulip body 200 (any variant), positioned to aligned with kerf split 360 which forms a pin guiding channel. When clamp 350 is moved distally or downwards (as viewed), pin 368 enters kerf split 360, and thereafter prevents radial rotation of clamp 350 with respect to tulip body 200. Additionally, a maximum downward projection of clamp 350 relative to tulip body 200 can be defined by a length of a segment of kerf 360 that is vertically aligned with pin 368, as shown in FIG. 27, enabling increased control of an extent of clamping forces, defining a limit of vertical movement, and blocking screw head 132 and clamp 350 from being pulled out of tulip body 200. Pins 368 can be press-fit into tulip 200, or can be attached by any other suitable means, such as threading, welding, or adhesive, as examples. In an embodiment, pins 368 are 0.45 mm wide by 1.8 mm long, although the size is dependent upon the size of tulip 200, clamp 350, kerf 360, and the forces to be withstood, and the type of metal or other material from which the respective components are fabricated.

With reference to FIG. 34, kerfs 360A, which divide clamp 350A in two portions, is provided with a narrower width "A", near the region of the saddle/clamp clip connection 352, and a wider width "B" along the remaining portion of kerf 360A. Width "A" can be sized to close completely first during compression, thereby defining a limit of compression of kerf 360A, and further limiting mechanical distortion, for example bowing, of clamp 350A and distortion of tulip body 200.

Embodiment 7—Clamp Kerfs

With reference to FIGS. 34-35, an additional relief cut or kerf 360B is formed in each clamp half of clamp 350, for example clamp 350A as shown, which enables further reduction of distortion, and particularly bowing, of clamp 350 and/or splaying of tulip arms 220, and enables better conformance to screw head 132. Kerfs 360B do not extend a complete height of clamp 350, thereby not separating clamp 350 into additional segments. Kerfs 360B can be formed in other orientations than the vertical orientation illustrated, for example at an angle from vertical, and can be longer or shorter, as determined for example by measured performance under various use conditions. Likewise additional or fewer kerfs 360B can be formed, as can be seen in FIG. 35, which contains additional kerfs 360C which begin at an upper periphery of clamp 350 and extend downwards, in contrast to kerfs 360B shown in FIG. 34, which extend upwards. By combining kerfs 360B which alternate in direction, in particular, additional flexibility is imparted to clamp 350, enabling better clamping strength due to greater conformity to screw head 132.

In an embodiment, there are only a plurality of kerfs 360B and no kerfs 360C, and in another embodiment there are only a plurality of kerfs 360C and no kerfs 360B. Similarly, kerfs 360A, which divide clamp 350 into segments, can be formed in the Z-shape shown in FIG. 30, or can have other shapes, or can be linear but extend at an angle with respect to an axial centerline of clamp 350. Kerfs 360A-C further facilitate forming an expanded clamp diameter as screw head 132 is passed into a clamp, and a contracted diameter as the clamp is engaged and compressed against screw head 132.

Embodiment 8—Blocking Flanges

With further reference to FIG. 35, and additional reference to FIGS. 36-37, clamp 350B includes a peripheral flange 372 extending from external peripheral ramp 354, which engages a mating flange 374 in tulip body 200E. As the overall diameter of clamp 350B is enlarged or expanded due to peripheral flange 372, clamp 350B is compressed to form a contracted diameter during installation and insertion into tulip body 200C, and thereafter rebounds to an uncontracted diameter, to thereby align flanges 372, 374 for engagement during clamping, as can be seen in FIG. 37.

When flanges 372 and 374 are engaged during clamping, clamp 350 is prevented from being pulled from within tulip body 200E. In the embodiment shown in FIGS. 35-37, increased pulling force does not result in a substantially increased clamping force, as flanges 372 and 374 are not ramped with respect to each other, but mutually engage on flat surfaces. Alternatively, flange 372A (shown diagrammatically) and flange 374A within tulip body 200F can be ramped to cause further compression, as shown in FIG. 38. In FIG. 38A, flanges 372B and 374B are illustrated diagrammatically and ramp in a reverse direction to that of FIG. 38, whereby flanges 372B and 374B form mutually engaging hooks or wedges. As with the flat ramps of FIG. 37, the embodiment of FIG. 38A does not cause further compression as a force pulls screw head 132 in a direction away from engagement with tulip body 200G, while providing an increased level of pull-out resistance.

An external surface of clamp 300 and/or an internal surface of tulip 200 can be anodized, polished, or otherwise be provided with a low friction coating to facilitate assembly and internal movement, while still maintaining a high dissociation load due to mechanical clamping. Similarly, and with further reference to FIG. 37, it may be seen that clamp clip portion 352B forms a curved upper surface that tangentially contacts saddle clip portion 352A (FIG. 37). This can serve to reduce a force needed to move flange 352B laterally during clamping, by decreasing friction from micro lateral motion and angulation between the surfaces of the saddle 150 and clamp 300. Further, the curved upper surface of clamp clip portion 352B forms a ramp which facilitates entry of clamp clip portion 352B into saddle clip portion clip portion 352A.

With reference to FIGS. 39-40, clamp 350C forms a clamp flange 372C, which can have any profile, including that of any variant of flange 372 herein, which cooperates with a mating tulip flange 374, as described for FIGS. 35-38A. However, flange 372C is formed from a free end 380 of a plurality of flexible digits 376, each attached at a fixed end 378 to the main body of the clamp 350C. A projection 382 extends inwards from free end 380 towards a central axis of clamp 350C. When screw head 132 enters clamp 350C, a peripheral surface of screw head 132 pushes projection 382, causing free end 380 to move away from the central axis, causing clamp flange 372C to project over tulip flange 374 (any corresponding variant), in a position as shown in FIGS. 35-38A. Flexible digits 376 thus configured are distributed about a periphery of clamp 372C to provide an even distribution of force. As shown in FIGS. 39-40, digits 376 can be cut from, or formed with, material of clamp 350, avoiding a need to attach additional material.

In FIG. 41, clamp 350 can be provided with a series of discrete peripheral projections 382 extending from clamp external peripheral ramp 354, and which collectively form a clamp flange 372D. Each has a profile of any of the types described for flanges 372 herein, and can be used with a tulip body 200 having a correspondingly shaped tulip flange 374.

Embodiment 9—Shear Ring

With reference to FIGS. 42-49, a screw head 132 is retained within tulip body 200G between a saddle 150B having an internal surface 408 shaped to complement an upper portion of screw head 132, and a shear ring 390 which engages a lower portion of screw head 132. A retaining ring 394 supports shear ring 390 and prevents shear ring 390 from moving out of an interior of tulip body 200G.

Shear ring 390 has a diameter which is less than the largest diameter of screw head 132, and less than the diameter of an opening formed by tulip distal ledge 242. In an embodiment, shear ring 390 can have a tapering interior profile 400 that corresponds to a shape of a lower portion of screw head 132. Shear ring 390 has a weakened area 392 that is solid but is more easily broken than a remainder of the ring.

Retaining ring 394 has a larger diameter than the largest diameter of screw head 132, and has a larger diameter than tulip distal ledge 242. Retaining ring can have an interior profile 402 corresponding to a shape of a lower surface of shear ring 390. Retaining ring 394 has a weakened point 396 which can be broken prior to assembly into tulip 200, or can be provided with a break along the periphery thereof, or retaining ring 394 can be provided in the form of a split ring (a spiral that visually appears as an integral ring).

With reference to FIGS. 46-49, a bone stabilizing assembly 100 including the foregoing parts is assembled, first, by bottom loading (as viewed) saddle 150B into tulip body 200G, and engaging saddle 150B at saddle detent portion 154B. Next, shear ring 390 is passed through distal ledge 242 and positioned within a lower ring chamber 398 of tulip 200G.

Retaining ring 394 can be assembled next by breaking weakened area 396 to form a free end, or otherwise passing a broken or free end of retaining ring 394 into ring chamber 398, and then threading/winding the remaining portion of retaining ring 394 into ring chamber 398. Shear ring 390 and retaining ring 394 are advantageously formed from a material that retains its original shape after bending, for example a shape memory alloy such as Nitinol, Cobalt Chromium (CoCr), or a titanium/aluminum/vanadium alloy (TAV), or other sufficiently durable and biocompatible metal.

In an alternative embodiment, retaining ring 394 is fabricated from a high density polymer or highly flexible metal, and is assembled as described above, or is alternatively distorted to be assembled into tulip body 200.

Retaining ring 394 has a larger diameter than tulip distal ledge 242 and is therefore retained within tulip body 200G. After assembly, shear ring 390 rests within a periphery defined by retaining ring interior profile 402, and is thereby likewise retained within tulip body 200G.

To engage screw 140, with reference to FIG. 48, a screw head is pushed into tulip body 200G in such a manner as to pass through retaining ring 394 to engage unbroken shear ring 390. As screw head 132 has a larger diameter than shear ring 390, a sufficient pressure exerted upon shear ring 390 breaks shear ring 390 at weakened area 392, enabling broken ring 390 to distort to allow screw head 132 to pass therethrough. Shear ring 390 is prevented from moving away from screw head 132 by an upper profile 406 of tulip ring chamber 398. Once screw head 132 has passed, shear ring 390 reforms a diameter smaller than screw head 132, and rests within retaining ring interior profile 402. Shear ring 390 is formed from a material selected for sufficient durability and flexibility to function as described.

Vertical wall portion 404 of ring interior profile 402 laterally engages shear ring 390 and prevents distortion of shear ring 390, particularly when screw head 132 is driven downwards in a direction of shear ring 390 and retaining ring 394 (FIG. 49), when locking cap is tightened, as described elsewhere herein. As shear ring 390 has reformed a diameter smaller than screw head 132, and as shear ring 390 is prevented from further distortion by retaining ring 390, screw head 132 is retained within tulip body 200G.

Embodiment 10—Spring Ring

Turning to FIGS. 50-56, a screw head 132 is retained within tulip body 200H between saddle 150B, described above and shown in FIG. 43, and spring ring 410 which engages a lower portion of screw head 132. A retaining ring 394A supports spring ring 410 and prevents spring ring 410 from moving out of an interior of tulip body 200H.

Spring ring 410 has a lower flange 412 which has a diameter which is less than the largest diameter of screw head 132. Retaining ring 394A can have a larger diameter than the largest diameter of screw head 132 and has a larger diameter than tulip distal ledge 242. Retaining ring 394A has an interior profile 402 corresponding to a shape of a lower surface of Spring ring 410. Spring ring 410 includes kerfs 360C which extend downwards (as viewed) along a portion of a height of spring ring 410, and kerfs 360B which extend upwards.

With reference to FIGS. 53-56, a bone stabilizing assembly 100 including the foregoing parts is assembled, first, by distal or bottom loading (as viewed) saddle 150B into tulip body 200H, and engaging saddle 150B at saddle detent portion 154B. Next, Spring ring 410 is passed through distal ledge 242. Lastly, retaining ring 394A is passed into tulip body 200H by placing free end 414 into tulip body 200H first, followed by threading/winding the remaining portion (FIG. 53). Retaining ring 394A has a larger diameter than tulip distal ledge 242 and is therefore retained within tulip body 200H. A lower end of spring ring 410 rests within a periphery defined by retaining ring interior profile 402A and is thereby likewise retained within tulip body 200H.

In FIG. 54, a screw head is pushed into tulip body 200H in such a manner as to pass through retaining ring 394 to engage spring ring 410. As screw head 132 has a larger diameter than spring ring lower flange 412, a pressure is exerted upon spring ring 410 to expand a diameter of spring ring 410 at lower flange 412, by expanding kerfs 360B. Concomitantly, kerfs 306C may be contracted, facilitating distortion of spring ring 410 to enable screw head 132 to pass above lower flange 412 and enter into an interior of spring ring 410 (FIG. 55).

Once screw head 132 has passed into spring ring 410, spring ring 410 resumes a former unexpanded or contracted diameter, and rests within retaining ring interior profile 402A. Spring ring 410 is formed from a material selected for sufficient durability and an ability to substantially resume a former shape after distortion due to passage of screw head 132.

A vertical wall portion 404 of ring interior profile 402A surrounds spring ring lower flange 412 and prevents re-expansion of spring ring lower flange 412, particularly when screw head 132 is driven downwards in a direction of spring ring 410 and retaining ring 394A (FIG. 56), when locking cap is tightened, as described elsewhere herein. As spring ring lower flange 412 has a diameter smaller than screw head 132, and as a diameter of spring ring 410 can no longer expand, screw head 132 is retained within tulip body 200H.

Embodiment 11—Retained Spring Clip

Referring now to FIGS. 57-63, a screw head 132 is retained within tulip body 200J between saddle 150B, described above, and spring ring 410A which engages a lower portion of screw head 132. A retaining ring 394A supports spring ring 410A and prevents spring ring 410A from moving out of an interior of tulip body 200H. Spring ring 410A is maintained in a deployment position by a ring detent 156 formed from a ring detent portion 156A and a second tulip detent 156B, which are otherwise as described with respect to detent 154, above. Ring detent is formed about some or all of a periphery of the tulip body and ring.

More particularly, spring ring 410A, which otherwise functions as described with respect to spring ring 410, above, forms a detent engagement between detent portions 156A and 156B, whereby spring ring 410A is maintained in a position at a proximal or upper end (as viewed) of an interior of tulip body 200J, while saddle 150B is likewise retained by detent 154 as described elsewhere herein. As such, an opening is maintained, and components are aligned, for insertion of screw head 132.

Spring ring 410A has a lower flange 412 which has a diameter which is less than the largest diameter of screw head 132. Retaining ring 394B can have a larger diameter than the largest diameter of screw head 132, and has a larger diameter than tulip distal ledge 242. Retaining ring 394B has an interior profile 402 corresponding to a shape of a lower surface of Spring ring 410A. Spring ring 410A includes kerfs 360C which extend downwards (as viewed) along a portion of a height of spring ring 410, and kerfs 360B which extend upwards.

With reference to FIGS. 60-61, a bone stabilizing assembly 100 including the foregoing parts is assembled, first, by bottom loading (as viewed) saddle 150B into tulip body 200J, and engaging saddle 150B at saddle detent portion 154B. Next, Spring ring 410A is passed through distal ledge 242. An internal ramp 416 is formed in an interior of tulip body 200J, upon which spring ring detent portion 156A slides and deflects inwards, which facilitates engagement of spring ring detent portions 156A with second tulip detent portion 156B. In this manner, a correct alignment of saddle 150B and spring ring 410A can be established prior to use, and can be reliably retained until insertion of screw head 132.

Lastly, retaining ring 394B is passed into tulip body 200J by placing free end 414 into tulip body 200J first, followed by threading/winding the remaining portion. Retaining ring 394B has a larger diameter than tulip distal ledge 242 and is therefore retained within tulip body 200J. A lower end of spring ring 410A is sized and dimensioned to rest within a periphery defined by retaining ring interior profile 402, when spring ring 410B is released from detent 156 during engagement of rod 180 by cap 160, as described elsewhere herein, after which spring ring 410A is thus captured by retaining ring 394B and cannot pass out of an interior of tulip body 200J.

Retaining ring 394B can now be contrasted with retaining ring 394A of FIGS. 50-56. More particularly, retaining ring vertical wall portion 404 of retaining ring 394A is taller than retaining ring vertical wall portion 404A of retaining ring 394B. This is achieved by lowering a portion of retaining ring 394A past tulip distal ledge 242. As such, by selecting a profile of retaining ring 404, a position of fastener 140 with respect to tulip body 200 can be adjusted, as best meets space and other therapeutic requirements. Variants 394, 394A or 394B can be substituted in the various embodiments herein where therapeutically beneficial.

As described with respect to FIG. 54, above, a screw head 132 is pushed into tulip body 200J in such a manner as to pass through retaining ring 394B to engage spring ring 410A. As tulip head 132 has a larger diameter than spring ring lower flange 412 (FIG. 58), a pressure is exerted upon spring ring 410A to expand a diameter of spring ring 410A at lower flange 412, by expanding/contracting kerfs 360B, 360C respectively. In addition, expansion of lower flange 412 and the distortion of spring ring 410A causes at least partial disengagement of detent 156, facilitating clamping via cap 160.

Once screw head 132 has passed into spring ring 410A, spring ring 410A resumes a former unexpanded or contracted diameter, and rests within retaining ring interior profile 402A. As can be seen in the figures, spring ring 410 and 410A have a lower ramped surface 418 which facilitates alignment with retaining ring 394A, 394B, respectively. FIGS. Spring ring 410A is formed from a material selected for sufficient durability and an ability to substantially resume a former shape after distortion due to passage of screw head 132.

Vertical wall portion 404A of ring interior profile 402A surrounds spring ring lower flange 412 (FIG. 58) and prevents re-expansion of spring ring lower flange 412, particularly when screw head 132 is driven downwards in a direction of spring ring 410A and retaining ring 394B (FIG. 63), when locking cap 160 is tightened, as described elsewhere herein. As spring ring lower flange 412 has a diameter smaller than screw head 132, and as a diameter of spring ring 410A can no longer expand, screw head 132 is retained within tulip body 200J.

Embodiment 12—Locking Clamp

Referring now to FIGS. 64-70, a screw head 132 is retained within tulip body 200K between saddle 150B, described above, and spring ring 410B which engages a lower portion of screw head 132. A retaining ring 394A supports spring ring 410B and prevents spring ring 410B from moving out of an interior of tulip body 200K. Spring ring 410B is maintained in a deployment position by a saddle/clamp clip connection 352.

More particularly, spring ring 410B includes ascending and descending kerfs 360B and 360C, enabling flexure in a manner similar to that described for spring rings 410 and 410B. Further spring ring 410B forms a clamp clip portion 352B having a ramped upper surface, similar to that of clip portion 352B of FIG. 37, and in contrast to that of FIG. 36. However, the various profiles of clamp clip portions 352A herein can be substituted.

Saddle 150A includes a ramped lower surface 422 which cooperates with the ramped upper surface of clip portion 352B to facilitate mutual engagement of spring ring 410B and saddle 150A. In the embodiment of FIGS. 64-70, ramped lower surface 422 is curved, and in the embodiment of FIG. 36 ramped lower surface 422 is flat, although these can be substituted, or another ramped profile can be provided.

By maintaining spring ring 410B in contact with saddle 150A, the latter maintained in position by saddle detent 154, an opening is maintained, and components are aligned, for insertion of screw head 132.

Spring ring 410B has an internally disposed lower profile 420 which has a diameter which is less than the largest diameter of screw head 132. Retaining ring 394A can have a larger diameter than the largest diameter of screw head 132, and has a larger diameter than tulip distal ledge 242. Retaining ring 394A has an interior profile 402 corresponding to a shape of a lower surface of Spring ring 410B.

With reference to FIG. 67, a bone stabilizing assembly 100 including the foregoing parts is assembled, first, by assembling spring ring 410B onto saddle 150A by engaging saddle/clip connection 352, then bottom loading (as viewed) the combination into tulip body 200K, and engaging saddle 150A with tulip detent portion 154A at saddle detent portion 154B. Alternatively, saddle 150A can be bottom loaded and engaged at saddle detent portion 154B first, followed by bottom loading spring ring 410B and then engaging saddle/clip connection 342.

Next, Spring ring 410B is passed through distal ledge 242, and the ramped upper surface of clamp clip portion 352B slides against ramped lower surface 422 of saddle 150A, resulting in engagement of saddle/clamp clip connection 352. In this manner, a correct alignment of saddle 150A and spring ring 410B can be established prior to use, and can be reliably retained until insertion of screw head 132.

Lastly, retaining ring 394A is passed into tulip body 200K by placing free end 414 into tulip body 200K first, followed by threading/winding the remaining portion. Retaining ring 394A has a larger diameter than tulip distal ledge 242 and is therefore retained within tulip body 200K. A lower end of spring ring 410B is sized and dimensioned to rest within a periphery defined by retaining ring interior profile 402, when saddle 150A is released from detent 154, together with attached spring ring 410B, during engagement of rod 180 by cap 160, as described elsewhere herein, after which spring ring 410B is thus captured by retaining ring 394A and cannot pass out of an interior of tulip body 200K.

As described with respect to FIG. 54, above, a screw head 132 is pushed into tulip body 200K in such a manner as to pass through retaining ring 394A to engage spring ring 410B. As tulip head 132 has a larger diameter than spring ring lower interior profile 420, a pressure is exerted upon spring ring 410B to expand a diameter of spring ring 410B at lower internal profile 420, by expanding/contracting kerfs 360B, 360C respectively.

Once screw head 132 has passed into spring ring 410B, spring ring 410B resumes a former unexpanded or contracted diameter, and rests within retaining ring interior profile 402A. Spring ring 410B is formed from a material selected for sufficient durability and an ability to substantially resume a former shape after distortion due to passage of screw head 132.

Vertical wall portion 404 of ring interior profile 402A surrounds a lower portion of spring ring 410B and prevents re-expansion of spring ring 410B, particularly when screw head 132 is driven downwards in a direction of spring ring 410B and retaining ring 394A (FIG. 70), when locking cap 160 is tightened, as described elsewhere herein. As spring ring 410B has a diameter smaller than screw head 132 at lower profile 422 at rest, and as a diameter of spring ring 410B at lower profile 422 can no longer expand due to engagement with retaining ring 394A, screw head 132 is retained within tulip body 200K.

Disassembly can be carried out by reversing the foregoing process. More particularly, cap 160 can be loosened, followed by pushing saddle 150A into saddle detent 154 by pushing tulip body 200K downwards onto screw head 132, followed by withdrawal of screw head 132 once the lower end of spring ring 410B is raised free of retaining ring 394A.

The bone stabilizing assemblies 100 of the disclosure allow for assembly of a modular head onto a pedicle screw after placement of the screw in the body, reducing implant prominence and improving ease of access to anatomy for discectomy, interbody placement, and osteotomy. The modular design also allows for multiple types of screw heads to be assembled to screws with varying functionality to increase versatility.

All references cited herein are expressly incorporated by reference in their entirety. There are many different features of the present disclosure and it is contemplated that these features may be used together or separately. Unless mention was made above to the contrary, it should be noted that all of the accompanying drawings are not to scale. Thus, the disclosure should not be limited to any particular combination of features or to a particular application of the disclosure. Further, it should be understood that variations and modifications within scope of the disclosure might occur to those skilled in the art to which the disclosure pertains. Accordingly, all expedient modifications readily attainable by one versed in the art from the disclosure set forth herein that are within the scope of the present disclosure are to be included as further embodiments of the present disclosure.

What is claimed is:

1. An orthopedic fixation system comprising:
a screw having a threaded shaft connected to a screw head by a neck portion, the screw extending from a proximal end to a distal end, the threaded shaft having first thread beginning near the distal end and extending to the neck portion, the threaded shaft further including a second thread beginning at a middle portion of the screw and extending to the neck portion;
a tulip defining a distal and proximal end and forming a tulip body forming an interior cavity,
two opposed arms extending away from a proximal end of the body,
cooperating threads disposed on mutually facing sides of each arm, and
a ledge positioned at a distal end of the tulip body at an entrance to the cavity;
a saddle defining a distal and proximal end, the saddle sized and dimensioned to be insertable into the tulip body,
forming a U shaped groove on the saddle proximal end sized to receive a spinal fixation rod inserted between the tulip arms, and
forming a curved surface on the saddle distal end sized and dimensioned to conformingly receive the screw head; and
a ring for engaging the screw head, the ring
positionable to form a first diameter smaller than the widest diameter of the screw head,
positionable to form a second diameter larger than the widest diameter of the screw head when the screw head is passed into the ring, and
positioned upon a proximal side of the tulip ledge;
the screw head clampable within the tulip body interior cavity in a position between the saddle and the ring when the saddle is urged in a distal direction towards the tulip ledge,
wherein the saddle is provided with locking prongs which move to a position interposed between half-clips and the tulip body when saddle is moved to the locked position,
wherein the half-clips are each provided with an inner screw head contacting surface which is shaped to mate with screw head to increase a contact area therebetween.

2. The device of claim 1, the saddle insertable into a distal end of the tulip body.

3. The device of claim 1, the tulip additionally forming a detent portion positioned distal to the threads upon an interior surface of the cavity, and the saddle additionally forming a detent portion mateable with the detent portion of the tulip to mutually releaseably connect the tulip and the saddle.

4. An orthopedic fixation system comprising:
a screw having a threaded shaft connected to a screw head by a neck portion, the screw extending from a proximal end to a distal end, the threaded shaft having first thread beginning near the distal end and extending to the neck portion, the threaded shaft further including a second thread beginning at a middle portion of the screw and extending to the neck portion;
a tulip defining a distal and proximal end and forming a tulip body forming an interior cavity, two opposed arms extending away from a proximal end
of the body, cooperating threads disposed on mutually facing sides
of each arm, and a ledge positioned at a distal end of the tulip body at an
entrance to the cavity;

a saddle defining a distal and proximal end, the saddle
sized and dimensioned to be insertable into the tulip
body, forming a U shaped groove on the saddle proximal end
sized to receive a spinal fixation rod inserted
between the tulip arms, and a ring for engaging the screw head, the ring
positionable to form a first diameter smaller than the
widest diameter of the screw head, the screw head clampable within the tulip body interior
cavity in a position between the saddle and the ring
when the saddle is urged in a distal direction towards
the tulip ledge, wherein the saddle is provided with locking prongs
which move to a position interposed between half-
clips and the tulip body when saddle is moved to the
locked position, wherein the half-clips are each provided with an inner
screw head contacting surface which is shaped to
mate with screw head to increase a contact area
therebetween.

\* \* \* \* \*